(12) United States Patent  
Zoller et al.

(10) Patent No.: US 8,357,698 B2
(45) Date of Patent: Jan. 22, 2013

(54) DIACYL INDAZOLE DERIVATIVES AS LIPASE AND PHOSPHOLIPASE INHIBITORS

(75) Inventors: Gerhard Zoller, Schoneck (DE); Stefan Petry, Kelkheim (DE); Gunter Muller, Sulzbach (DE); Hubert Heuer, Schwabenheim (DE); Norbert Tennagels, Siegburg (DE)

(73) Assignee: Sanofi, Paris (FR)

( * ) Notice: Subject to any disclaimer, the term of this patent is extended or adjusted under 35 U.S.C. 154(b) by 226 days.

(21) Appl. No.: 12/839,863

(22) Filed: Jul. 20, 2010

(65) Prior Publication Data

US 2010/0286133 A1    Nov. 11, 2010

Related U.S. Application Data

(60) Division of application No. 12/099,337, filed on Apr. 8, 2008, now Pat. No. 7,772,268, which is a continuation of application No. PCT/EP2006/009577, filed on Oct. 4, 2006.

(30) Foreign Application Priority Data

Oct. 12, 2005    (DE) .................. 10 2005 048 897

(51) Int. Cl.
*C07D 487/04* (2006.01)
*A61K 31/4375* (2006.01)

(52) U.S. Cl. .................. 514/303; 546/119; 546/120

(58) Field of Classification Search .................. 546/119, 546/120; 514/303
See application file for complete search history.

(56) References Cited

U.S. PATENT DOCUMENTS 7,968,719 B2 * 6/2011 Zoller et al. .................. 546/119

FOREIGN PATENT DOCUMENTS

| EP | 1164421 | 12/2001 |
|---|---|---|
| WO | WO 03/035005 | 5/2003 |
| WO | WO 2004/035550 | 4/2004 |
| WO | WO 2004/037814 | 5/2004 |
| WO | WO 2004/093872 | 11/2004 |
| WO | WO 2005/073199 | 8/2005 |

* cited by examiner

*Primary Examiner* — Kahsay T Habte
(74) *Attorney, Agent, or Firm* — Barbara E. Kurys; Scully, Scott, Murphy & Presser, P.C.

(57) ABSTRACT

The invention relates to diacyl indazole derivatives of general formulae (I) or (II) and to the pharmaceutically acceptable salts thereof:

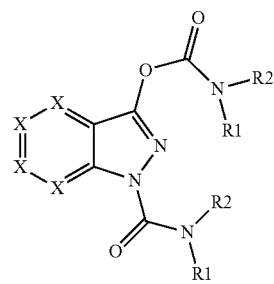

(I)

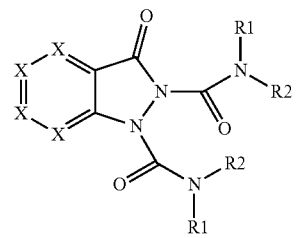

(II)

Wherein X, R1 and R2 are as defined herein. The invention also relates to the use of these compounds to treat diabetes mellitus, dyslipidemia and atherosclerotic disorders.

16 Claims, No Drawings

DIACYL INDAZOLE DERIVATIVES AS LIPASE AND PHOSPHOLIPASE INHIBITORS

This application is a divisional of U.S. Ser. No. 12/099,337 filed Apr. 8, 2008 now U.S. Pat. No. 7,772,268 which is a continuation of International application No. PCT/EP2006/009,577, filed Oct. 4, 2006, which is incorporated herein by reference in its entirety; which claims the benefit of priority of German Patent Application No. 102005048897.8, filed Oct. 12, 2005.

The present invention relates to diacylindazole derivatives of the formulae I or II, to their pharmaceutically usable salts and to their use as medicinal substances.

Compounds of similar structure are described in WO 2005/073199. The prior art also includes WO2003/035005.

It is an object of the present invention to provide alternative compounds which bring about an inhibition of hormone-sensitive lipase or of endothelial lipase.

The invention relates to diacylindazole derivatives of the formulae I or II,

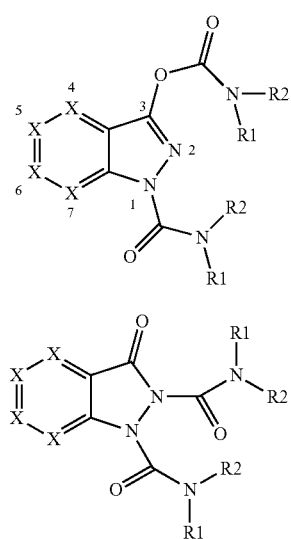

where the meanings are:
X identically or differently =C(—R)— or =N—, where not more than two X are =N—;
R identically or differently hydrogen, halogen, $(C_1$-$C_6)$-alkyl, $(C_1$-$C_3)$-alkyloxy-$(C_1$-$C_3)$-alkylene, $(C_1$-$C_3)$-haloalkyl, hydroxy, $(C_1$-$C_6)$-alkyl-mercapto, amino, $(C_1$-$C_6)$-alkylamino, di-$(C_2$-$C_{12})$-alkylamino, mono-$(C_1$-$C_6)$-alkylaminocarbonyl, di-$(C_2$-$C_8)$-alkylaminocarbonyl, COOR3, cyano, $(C_1$-$C_6)$-alkylsulfonyl, $(C_1$-$C_6)$-alkylsulfinyl, aminosulfonyl, nitro, pentafluorosulfanyl, phenyl, heterocycle, phenoxy, O-heterocycle, CO—NR6R7, O—CO—NR6R7, O—CO—$(C_1$-$C_6)$-alkylene-CO—O—$(C_1$-$C_6)$-alkyl, O—CO—$(C_1$-$C_6)$-alkylene-CO—OH, O—CO—$(C_1$-$C_6)$-alkylene-CO—NR6R7 or unsubstituted or mono- or poly-F-substituted $(C_1$-$C_6)$-alkyloxy;
R1 identically or differently $(C_5$-$C_{16})$-alkyl, $(C_3$-$C_{12})$-cycloalkyl, Y-aryl, Y-heterocycle or bicycle, where cycloalkyl, aryl, heterocycle or bicycle may be substituted one or more times by halogen, $(C_1$-$C_6)$-alkyl, $(C_1$-$C_3)$-alkyloxy, hydroxy, $(C_1$-$C_6)$-alkylmercapto, amino, $(C_1$-$C_6)$-alkylamino, di-$(C_2$-$C_{12})$-alkylamino, mono-$(C_1$-$C_6)$-alkylaminocarbonyl, di-$(C_2$-$C_8)$-alkylaminocarbonyl, $(C_1$-$C_6)$-alkyloxycarbonyl, $(C_1$-$C_6)$-alkylcarbonyl, cyano, trifluoromethyl, trifluoromethyloxy, $(C_1$-$C_6)$-alkylsulfonyl, aminosulfonyl, nitro;
Y $(C_1$-$C_3)$-alkyl, which may be substituted one or more times by halogen, $(C_1$-$C_3)$-alkyl, hydroxy or trifluoromethyl;
R2 hydrogen; or
R1 and R2 together with the nitrogen atom carrying them form a monocyclic, saturated or partly unsaturated 4- to 7-membered ring system or a bicyclic saturated or partly unsaturated 8- to 14 membered ring system whose individual members of the ring systems may be replaced by one to three atoms or atomic groups from the series —CHR4-, —CR4R5-, —(C=R4)-, —NR4-, —C(=O)—, —O—, —S—, —SO—, —SO$_2$—, with the proviso that two units from the series —O—, —S—, —SO—, —SO$_2$— may not be adjacent;
R3 hydrogen, $(C_1$-$C_6)$-alkyl, benzyl;
R4, R5 identically or differently $(C_1$-$C_6)$-alkyl, halogen, trifluoromethyl, phenyl, heterocycle, COOR3, $(C_3$-$C_{12})$-cycloalkyl;
R6, R7 identically or differently hydrogen, $(C_1$-$C_6)$-alkyl, phenyl, benzyl, $(C_3$-$C_{12})$-cycloalkyl;
the tautomeric forms of the compounds and the physiologically tolerated salts thereof,
with the proviso that not more than one R is phenyl or heterocycle.

Preference is given to compounds of the formulae I or II in which the meanings are
X identically or differently =C(—R)— or =N—, where not more than one X is =N—;
R identically or differently hydrogen, halogen, $(C_1$-$C_6)$-alkyl, hydroxy, $(C_1$-$C_3)$-alkyloxy, amino, COOR3, trifluoromethyl, $(C_1$-$C_6)$-alkylsulfonyl, nitro, pentafluorosulfanyl, phenyl, $(C_5$-$C_7)$-heterocycle, CO—NR6R7, O—CO—NR6R7 or O—CO—$(C_1$-$C_6)$-alkylene-CO—O—$(C_1$-$C_6)$-alkyl;
R1 identically or differently $(C_6$-$C_{10})$-alkyl, $(C_6$-$C_{12})$-cycloalkyl, Y-phenyl, Y-heterocycle or bicycle, where cycloalkyl, phenyl, heterocycle or bicycle may be substituted one or more times by halogen, $(C_1$-$C_6)$-alkyl, $(C_1$-$C_3)$-alkyloxy, hydroxy, $(C_1$-$C_6)$-alkylmercapto, amino, $(C_1$-$C_6)$-alkylamino, di-$(C_2$-$C_{12})$-alkylamino, mono-$(C_1$-$C_6)$-alkylaminocarbonyl, di-$(C_2$-$C_8)$-alkylaminocarbonyl, $(C_1$-$C_6)$-alkyloxycarbonyl, $(C_1$-$C_6)$-alkylcarbonyl, cyano, trifluoromethyl, trifluoromethyloxy, $(C_1$-$C_6)$-alkylsulfonyl, aminosulfonyl, nitro;
Y —CH$_2$—, which may be substituted once by fluorine, methyl or hydroxy;
R2 hydrogen; or
R1 and R2 together with the nitrogen atom carrying them form a monocyclic, saturated 5- to 6-membered ring system or a bicyclic saturated or partly unsaturated 9- to 10-membered ring system, whose individual members of the ring systems may be replaced by one to three atoms or atomic groups from the series —CHR4-, —CR4R5-, —(C=R4)-, —NR4-, —O—, —S—, with the proviso that two units from the series —O—, —S— may not be adjacent;
R3 hydrogen, $(C_1$-$C_6)$-alkyl, benzyl;
R4, R5 identically or differently $(C_1$-$C_6)$-alkyl, halogen, trifluoromethyl, COOR3, $(C_3$-$C_7)$-cycloalkyl, phenyl, heterocycle;
R6, R7 identically or differently hydrogen, $(C_1$-$C_6)$-alkyl, phenyl, benzyl, $(C_3$-$C_{12})$-cycloalkyl;
the tautomeric forms of the compounds and the physiologically tolerated salts thereof, with the proviso that not more than one R is phenyl or ($C_5$-$C_7$)-heterocycle.

Particular preference is given to compounds of the formulae I or II in which the meanings are X identically or differently =C(—R)— or =N—, where not more than one X is =N—;

R identically or differently hydrogen, halogen, hydroxy, ($C_1$-$C_6$)-alkyl, trifluoromethyl, ($C_1$-$C_3$)-alkyloxy or amino;

R1 identically or differently ($C_6$-$C_{10}$)-alkyl, ($C_6$-$C_{12}$)-cycloalkyl, Y-phenyl, Y-heterocycle, where cycloalkyl, phenyl, or heterocycle may be substituted one or more times by halogen, ($C_1$-$C_6$)-alkyl, ($C_1$-$C_3$)-alkyloxy, hydroxy, amino, trifluoromethyl, trifluoromethyloxy;

Y —$CH_2$—;

R2 hydrogen; or

R1 and R2 together with the nitrogen atom carrying them may form a monocyclic, saturated 5- to 6-membered ring system or a bicyclic saturated or partly unsaturated 9- to 10-membered ring system, whose individual members of the ring systems may be replaced by one to three atoms or atomic groups from the series —CHR4-, —CR4R5-, —(C=R4)-, —NR4-, —O—, —S—, with the proviso that two units from the series —O—, —S— may not be adjacent;

R3 hydrogen, ($C_1$-$C_6$)-alkyl, benzyl;

R4, R5 identically or differently ($C_1$-$C_6$)-alkyl, halogen, trifluoromethyl, COOR3, ($C_3$-$C_7$)-cycloalkyl, phenyl, ($C_5$-$C_7$)-heterocycle;

the tautomeric forms of the compounds and the physiologically tolerated salts thereof.

Very particular preference is given to the compounds of the formulae I or II, in which X is identically or differently =C(—R)— or =N—, where not more than one X is =N—;

R is identically or differently hydrogen, halogen, hydroxy, ($C_1$-$C_6$)-alkyl, trifluoromethyl, ($C_1$-$C_3$)-alkyloxy or amino;

R1 is identically or differently ($C_6$-$C_{10}$)-alkyl or Y-phenyl, which may be substituted by halogen, ($C_1$-$C_6$)-alkyl, ($C_1$-$C_3$)-alkyloxy or trifluoromethyl;

Y is $CH_2$;

R2 is hydrogen; or

R1 and R2 together with the nitrogen atom carrying them form a monocyclic, saturated 5- to 6-membered ring system, whose individual members may be replaced by one to three atoms or atomic groups from the series —CHR4-, —NR4-, —O—, —S—, with the proviso that two units from the series —O—, —S—, may not be adjacent;

R4 is ($C_1$-$C_6$)-alkyl, cyclopropyl, trifluoromethyl or phenyl;

the tautomeric forms of the compounds and the physiologically tolerated salts thereof.

Particular preference is also given to the compounds of the formulae I or II in which NR1R2 is a monocyclic, saturated 5- to 6-membered ring system which contains an atom or atomic member from the series —CHR4-, —CR4R5-, —(C=R4)-, —NR4-, —O—, —S— in position 4.

Very particular preference is given in particular to the compounds of the formulae I or II in which X is identically or differently =C(—R)— or =N—, where not more than one X is =N—;

R is identically or differently hydrogen, F, Cl, hydroxy, methyl, trifluoromethyl or amino;

R1 is identically or differently ($C_6$-$C_{10}$)-alkyl or Y-phenyl, which may be substituted by methyl;

Y is $CH_2$;

R2 is hydrogen; or

R1 and R2 together with the nitrogen atom carrying them form a monocyclic, saturated 5- to 6-membered ring system, whose individual members may be replaced by one to three atoms or atomic groups from the series —CHR4-, —NR4-, —O—, —S—, with the proviso that two units from the series —O—, —S— may not be adjacent; or form a bicyclic, partly unsaturated 9- to 10-membered ring system in which one member may be replaced by —S—;

R4 is methyl, trifluoromethyl or phenyl which may be substituted once or twice by methyl or Cl;

the tautomeric forms of the compounds and the physiologically tolerated salts thereof.

Particular preference is also given to the compounds of the formulae I or II in which R1 and R2 together with the nitrogen atom carrying them may form a monocyclic, saturated 5- to 6-membered ring system or a bicyclic saturated or partly unsaturated 9- to 10 membered ring system, whose individual members of the ring systems may be replaced by an atom or atomic group from the series —CHR4-, —NR4.

Further preference is given to compounds of the formulae I or II in which

X is identically or differently =C(—R)—.

A further preferred embodiment are compounds of the formulae I or II in which

X is identically or differently =C(—R)— or =N—, where one X is =N—.

Preference is also given to the compounds of the formulae I or II in which

X in position 4, 5 and 6 is identically or differently =C(—R)—, and in position 7 is =N—.

Preference is further given to compounds of the formulae I or II in which

X in position 4, 5 and 7 is =C(—R)— with R=hydrogen, and in position 6 R is not hydrogen.

The invention relates to compounds of the formulae I or II in the form of their salts, racemates, racemic mixtures and pure enantiomers, and to their diastereomers and mixtures thereof.

The alkyl radicals in the substituents R, R1, R2, R3, R4, R5, R6 and R7 may be both straight-chain and branched. Halogen is fluorine, chlorine, bromine or iodine, in particular fluorine or chlorine.

Haloalkyl are alkyl radicals in which one, more than one or all hydrogen atoms are replaced by halogen, preferably fluorine.

An aryl radical means a phenyl or naphthyl radical.

The aryl radicals may be substituted one or more times by suitable groups such as, for example: F, Cl, Br, I, $CF_3$, $NO_2$, CN, COOH, COO($C_1$-$C_6$)alkyl, $CONH_2$, CONH($C_1$-$C_6$)alkyl, CON[($C_1$-$C_6$)alkyl]$_2$, ($C_3$-$C_{10}$)-cycloalkyl, ($C_1$-$C_{10}$-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$- heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$-$SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—

($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl-COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl-COO-aryl, N($C_1$-$C_6$)-alkyl-COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N (($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to three times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

Heterocycle is a mono- or bicyclic ring system having 5 to 12 ring members, in which at least one atom in the ring system is a heteroatom from the series N, O and S. This definition also includes ring systems in which the heterocycle is fused to a benzene nucleus. ($C_5$-$C_7$)-Heterocycle is a monocyclic, and ($C_8$-$C_{12}$)-heterocycle is a bicyclic ring system.

Suitable "heterocyclic rings" or "heterocyclic radicals" are azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl stands both for 2-, 3- and 4-pyridyl. Thienyl stands both for 2- and 3-thienyl. Furyl stands both for 2- and 3-furyl.

Also included are the corresponding N-oxides of these compounds, i.e. for example 1-oxy-2-, 3- or 4-pyridyl.

The heterocyclic rings or heterocyclic radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, ($C_1$-$C_6$)-alkyl, ($C_2$-$C_6$)-alkenyl, ($C_2$-$C_6$)-alkynyl, O—($C_1$-$C_6$)-alkyl, where one, more than one or all hydrogen(s) in the alkyl radicals may be replaced by fluorine;
$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-phenyl, SO—($C_1$-$C_6$)-alkyl, SO—($CH_2$)$_n$-phenyl, $SO_2$—($C_1$-$C_6$)-alkyl, $SO_2$—($CH_2$)$_n$-phenyl, where n may be 0-6, and the phenyl radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;
C(NH)($NH_2$), $NH_2$, NH—($C_1$-$C_6$)-alkyl, N(($C_1$-$C_6$)-alkyl)$_2$, NH($C_1$-$C_7$)-acyl, phenyl, O—($CH_2$)$_n$-phenyl, where n may be 0-6, where the phenyl ring may be substituted one to three times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

A cycloalkyl radical means a ring system which comprises one or more rings, which is in saturated or partially unsaturated (with one or two double bonds) form, and which is composed exclusively of carbon atoms, such as, for example, cyclopropyl, cyclopentyl, cyclopentenyl, cyclohexyl or adamantyl.

The cycloalkyl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;
$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$-$SO_2$—N(($CH_2$)$_n$-(heterocycle)$_2$
where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;
C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl-CO—($C_1$-$C_6$)-alkyl, N($C_1$-$C_6$)-alkyl-COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl-COO-aryl, N($C_1$-$C_6$)-alkyl-COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to three times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, COOH, COO—($C_1$-$C_6$)-alkyl, $CONH_2$.

Bicycle is a partly unsaturated bicyclic ring system which has 8 to 14 ring members and has exclusively carbon atoms as ring members. Examples which may be mentioned are the tetrahydronaphthyl, alpha- or beta-tetralone, indanyl or indan-1-onyl radical. Preferred bicyclic radicals are tetrahydronaphthyl and indanyl.

The bicyclic radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;
$PO_3H_2$, $SO_3H$, $SO_2$—$NH_2$, $SO_2NH(C_1$-$C_6)$-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—$NH(CH_2)_n$-aryl, $SO_2$—$NH(CH_2)_n$-heterocycle, $SO_2$—$N(C_1$-$C_6)$-alkyl)($CH_2$)$_n$-aryl, $SO_2$—$N(C_1$-$C_6)$-alkyl)($CH_2$)$_n$-heterocycle, $SO_2$—$N((CH_2)_n$-aryl)$_2$-$SO_2$—$N((CH_2)_n$-heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; $C(NH)(NH_2)$, $NH_2$, NH—($C_1$-$C_6$)-alkyl, N(($C_1$-$C_6$)-alkyl)$_2$, $NH(C_1$-$C_7)$-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, $N(C_1$-$C_6)$-alkyl —CO—($C_1$-$C_6$)-alkyl, $N(C_1$-$C_6)$-alkyl-COO—($C_1$-$C_6$)-alkyl, $N(C_1$-$C_6)$-alkyl —CO-aryl, $N(C_1$-$C_6)$-alkyl —CO-heterocycle, $N(C_1$-$C_6)$-alkyl —COO-aryl, $N(C_1$-$C_6)$-alkyl —COO-heterocycle, $N(C_1$-$C_6)$-alkyl —CO—NH—($C_1$-$C_6$)-alkyl), $N(C_1$-$C_6)$-alkyl —CO—NH-aryl, $N(C_1$-$C_6)$-alkyl —CO—NH-heterocycle, $N((C_1$-$C_6)$-alkyl)-CO—N—($C_1$-$C_6$)-alkyl)$_2$, $N((C_1$-$C_6)$-alkyl)-CO—N(($C_1$-$C_6)$-alkyl)-aryl, $N((C_1$-$C_6)$-alkyl)-CO—N(($C_1$-$C_6)$-alkyl)-heterocycle, $N((C_1$-$C_6)$-alkyl)-CO—N-(aryl)$_2$, $N((C_1$-$C_6)$-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6)$-alkyl)-aryl, N(heterocycle)-CO—N(($C_1$-$C_6)$-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to three times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, COOH, COO—($C_1$-$C_6$)-alkyl, $CONH_2$.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the invention of the formulae I or II, for example an ester, which on administration to a mammal such as, for example, a human is able to form (directly or indirectly) compounds of the formulae I or II or an active metabolite thereof.

Physiologically functional derivatives also include prodrugs of the compounds of the invention as, for example, described in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formulae I or II" hereinafter refer to compound(s) of the formulae I or II as described above, and their salts, solvates and physiologically functional derivatives as described herein.

Use

The compounds of the invention of the formulae I or II have a surprising inhibitory effect on hormone sensitive lipase, HSL, an allosteric enzyme in adipocytes which is inhibited by insulin and is responsible for the breakdown of fats in fat cells and thus for transferring fat constituents into the blood stream. Inhibition of this enzyme is therefore equivalent to an insulin-like effect of the compounds of the invention, eventually leading to a reduction of free fatty acids in the blood and of blood glucose. They can therefore be employed for metabolic derangements such as, for example, for non-insulin-dependent diabetes mellitus, for diabetic syndrome and for direct pancreatic damage.

The compounds of the invention of the formulae I or II may additionally have an inhibitory effect on endothelial lipase (EL). The preferred substrate for EL is HDL, which has antiatherosclerotic activity. A reduction in the HDL level leads to progression of atherosclerosis and its sequelae such as metabolic syndrome and coronary heart disease. An inhibition of EL should thus lead to prevention of atherosclerotic disorders.

It has further been found that the inhibitory effect of the compounds of the invention of the formulae I or II is selective in relation to other lipases.

Compounds of this type are particularly suitable for the treatment and/or prevention of 1.—Disorders of fatty acid metabolism and glucose utilization disorders
2. Disorders of the insulin sensitivity of myo-, adipo- and hepatocytes (insulin resistance)-metabolic syndrome.
3. Diabetes mellitus, especially type 2 diabetes, including the prevention of the sequelae associated therewith.

Particular aspects in this connection are
hyperglycemia,
improvement in insulin resistance,
improvement in glucose tolerance,
protection of the pancreatic β cells
prevention of macro- and microvascular disorders
4. Dyslipidemias and their sequelae such as, for example, atherosclerosis, coronary heart disease, cerebrovascular disorders etc, especially those (but not restricted thereto) which are characterized by one or more of the following factors:
high plasma triglyceride concentrations, high postprandial plasma triglyceride concentrations,
low HDL cholesterol concentration
low apoA lipoprotein concentrations
high LDL cholesterol concentrations
small dense LDL cholesterol particles
high apoB lipoprotein concentrations
5. Various other conditions which may be associated with the metabolic syndrome, such as:
obesity (excess weight), including central obesity
thromboses, hypercoagulable and prothrombotic stages (arterial and venous)
high blood pressure
heart failure such as, for example (but not restricted thereto), following myocardial infarction, hypertensive heart disease or cardiomyopathy
6. Other disorders or conditions in which inflammatory reactions or cell differentiation is for example involved are:
atherosclerosis such as, for example (but not restricted thereto), coronary sclerosis including angina pectoris or myocardial infarction, stroke
vascular restenosis or reocclusion
chronic inflammatory bowel diseases such as, for example, Crohn's disease and ulcerative colitis
pancreatitis
other inflammatory states
retinopathy
adipose cell tumors
adipose cell carcinomas such as, for example, liposarcomas
solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
acute and chronic myeloproliferative disorders and lymphomas
angiogenesis
neurodegenerative disorders
Alzheimer's disease
multiple sclerosis
Parkinson's disease
erythemato-squamous dermatoses such as, for example, psoriasis
acne vulgaris
other skin disorders and dermatological conditions which are modulated by PPAR
eczemas and neurodermatitis
dermatitis such as, for example, seborrheic dermatitis or photodermatitis
keratitis and keratoses such as, for example, seborrheic keratoses, senile keratoses, actinic keratosis, photo-induced keratoses or keratosis follicularis
keloids and keloid prophylaxis
warts, including condylomata or condylomata acuminata
human papilloma viral (HPV) infections such as, for example, venereal papillomata, viral warts such as, for example, molluscum contagiosum, leukoplakia
papular dermatoses such as, for example, lichen planus
skin cancer such as, for example, basal-cell carcinomas, melanomas or cutaneous T-cell lymphomas
localized benign epidermal tumors such as, for example, keratoderma, epidermal naevi
chilblains
high blood pressure
syndrome X
polycystic ovary syndrome (PCOS)
asthma
osteoarthritis
lupus erythematosus (LE) or inflammatory rheumatic disorders such as, for example, rheumatoid arthritis
vasculitis
wasting (cachexia)
gout
ischemia/reperfusion syndrome
acute respiratory distress syndrome (ARDS)

Formulations

The amount of a compound of the invention necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg. For the therapy of the abovementioned conditions, the compounds of formulae I or II may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of the invention. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compounds of formulae I or II used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formulae I or II; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formulae I or II with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of compounds of formulae I or II, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formulae I or II with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formulae I and II are distinguished by favorable effects on metabolic disorders. They beneficially influence lipid and sugar metabolism, in particular they lower the triglyceride level and are suitable for the prevention and treatment of type II diabetes and arteriosclerosis and the diverse sequelae thereof.

Combinations with Other Medicaments

The compounds of the invention can be administered alone or in combination with one or more further pharmacological active ingredients. In particular, the compounds of the invention can be administered with active ingredients which have a similar pharmacological effect to themselves. For example they can be administered in combination with active ingredients which have favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.
11. active ingredients for the treatment of neurodegenerative diseases
12. active ingredients for the treatment of diseases of the central nervous system
13. active ingredients for the treatment of dependence on drugs, nicotine and alcohol
14. analgesics They can be combined with the compounds of the invention of the formulae I or II in particular for a synergistic improvement in the effect. Administration of the active ingredient combination can take place either by separate administration of the active ingredients to the patient or in the form of combination products in which a plurality of active ingredients are present in one pharmaceutical preparation.

Further active ingredients particularly suitable for the combination products are: All antidiabetics which are mentioned in the Rote Liste 2006, chapter 12; all weight-reducing agents/appetite suppressants which are mentioned in the Rote Liste 2006, chapter 1; all lipid-lowering agents which are mentioned in the Rote Liste 2006, chapter 58. They can be combined with the compound of the invention of the formulae I or II in particular for a synergistic improvement in the effect. Administration of the active ingredient combination can take place either by separate administration of the active ingredients to the patient or in the form of combination products in which a plurality of active ingredients are present in one pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964 or those described in WO 2005/005477 (Novo Nordisk), fast-acting insulins (see U.S. Pat. No. 6,221,633), inhalable insulins such as, for example, Exubera or oral insulins such as, for example, IN-105 (Nobex) or Oral-lyn™ (Generex Biotechnology), GLP-1-derivatives such as, for example, exenatide, liraglutide or those which have been disclosed in WO 98/08871 or WO 2005/027978 of Novo Nordisk A/S, in WO 01/04156 of Zealand or in WO 00/34331 of Beaufour-Ipsen, Pramlintide Acetate (Symlin; Amylin Pharmaceuticals), and orally effective hypoglycemic active ingredients.

The active ingredients include preferably
sulfonylureas,
biguanides,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of glucose transporter 4 (GLUT4),
inhibitors of glutamine-fructose-6-phosphate amidotransferase (GFAT),
GLP-1 agonists,
potassium channel openers such as, for example, those which have been disclosed in WO 97/26265 and WO 99/03861 of Novo Nordisk A/S,
inhibitors of dipeptidylpeptidase IV (DPP-IV),
insulin sensitizers,
inhibitors of liver enzymes involved in stimulating gluconeogenesis and/or
glycogenolysis,
modulators of glucose uptake, of glucose transport and of glucose reabsorption, inhibitors of 11β-HSD1,
inhibitors of protein tyrosine phosphatase 1B (PTP1B),
modulators of the sodium-dependent glucose transporter 1 or 2 (SGLT1, SGLT2), compounds which alter lipid metabolism such as antihyperlipidemic active ingredients and antilipidemic active ingredients,
compounds which reduce food intake,
compounds which increase thermogenesis,
PPAR and RXR modulators and
active ingredients which act on the ATP-dependent potassium channel of the beta cells.

In one embodiment of the invention, the compound of the formula I or II is administered in combination with an HMG-CoA reductase inhibitor such as simvastatin, fluvastatin, pravastatin, lovastatin, atorvastatin, cerivastatin, rosuvastatin or L-659699.

In one embodiment of the invention, the compound of the formula I or II is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO 2005/042692), MD-0727 (Microbia Inc., WO 2005/021497) or with compounds as described in WO 2002/066464 (Kotobuki Pharmaceutical Co. Ltd.), WO 2005/062824 (Merck & Co.) or WO 2005/061451 and WO 2005/061452 (AstraZeneca AB).

In one embodiment of the invention, the compound of the formula I or II is administered in combination with a PPAR gamma agonist such as, for example, rosiglitazone, pioglitazone, JTT-501, GI 262570, R-483 or CS-011 (rivoglitazone).

In one embodiment of the invention, the compound of the formula I or II is administered in combination with a PPAR alpha agonist such as, for example, GW9578, GW-590735, K-111, LY-674, KRP-101 or DRF-10945.

In one embodiment of the invention, the compound of the formula I or II is administered in combination with a mixed PPAR alpha/gamma agonist such as, for example, muraglitazar, tesaglitazar, naveglitazar, LY-510929, ONO-5129, E-3030 or as described in WO 00/64888, WO 00/64876, WO 03/020269, WO 2004/075891, WO 2004/076402, WO 2004/075815, WO 2004/076447, WO 2004/076428, WO 2004/076401, WO 2004/076426, WO 2004/076427, WO 2006/018118, WO 2006/018115, and WO 2006/018116 or in J. P. Berger et al., TRENDS in Pharmacological Sciences 28(5), 244-251, 2005.

In one embodiment of the invention, the compound of the formula I or II is administered in combination with a PPAR delta agonist such as, for example, GW-501516, or as described in WO 2005/097762, WO 2005/097786, WO2005/097763, WO 2006/029699.

In one embodiment of the invention, the compound of the formula I or II is administered in combination with metaglidasen or with MBX-2044 or other partial PPAR gamma agonists/antagonists.

In one embodiment of the invention, the compound of the formula I or II is administered in combination with a fibrate such as, for example, fenofibrate, clofibrate or bezafibrate.

In one embodiment of the invention, the compound of the formula I or II is administered in combination with an MTP inhibitor such as, for example, implitapide, BMS-201038, R-103757 or those described in WO 2005/085226.

In one embodiment of the invention, the compound of the formula I or II is administered in combination with a CETP inhibitor such as, for example, torcetrapib or JTT-705.

In one embodiment of the invention, the compound of the formula I or II is administered in combination with a bile acid absorption inhibitor (see, for example, U.S. Pat. No. 6,245,744, U.S. Pat. No. 6,221,897 or WO 00/61568), such as, for example, HMR 1741 or those as described in DE 10 2005 033099.1 and DE 10 2005 033100.9.

In one embodiment of the invention, the compound of the formula I or II is administered in combination with a polymeric bile acid adsorbent such as, for example, cholestyramine or colesevelam.

In one embodiment of the invention, the compound of the formula I or II is administered in combination with an LDL receptor inducer (see U.S. Pat. No. 6,342,512), such as, for example, HMR1171, HMR1586 or those as described in WO 2005/097738.

In one embodiment, the compound of the formula I or II is administered in combination with Omacor® (Omega-3 fatty acids; highly concentrated ethyl esters of eicosapentaenoic acid and of docosahexaenoic acid).

In one embodiment of the invention, the compound of the formula I or II is administered in combination with an ACAT inhibitor such as, for example, avasimibe.

In one embodiment of the invention, the compound of the formula I or II is administered in combination with an antioxidant such as, for example, OPC-14117, probucol, tocopherol, ascorbic acid, β-carotene or selenium.

In one embodiment of the invention, the compound of the formula I or II is administered in combination with a vitamin such as, for example, vitamin B6 or vitamin B12.

In one embodiment of the invention, the compound of the formula I or II is administered in combination with a lipoprotein lipase modulator such as, for example, ibrolipim (NO-1886).

In one embodiment of the invention, the compound of the formula I or II is administered in combination with an ATP citrate lyase inhibitor such as, for example, SB-204990.

In one embodiment of the invention, the compound of the formula I or II is administered in combination with a squalene synthetase inhibitor such as, for example, BMS-188494 or as described in WO 2005/077907.

In one embodiment of the invention, the compound of the formula I or II is administered in combination with a lipoprotein(a) antagonist such as, for example, gemcabene (CI-1027).

In one embodiment of the invention, the compound of the formula I or II is administered in combination with an HM74A receptor agonist such as, for example, nicotinic acid.

In one embodiment of the invention, the compound of the formula I or II is administered in combination with a lipase inhibitor such as, for example, orlistat or cetilistat (ATL-962).

In one embodiment of the invention, the compound of the formula I or II is administered in combination with insulin.

In one embodiment of the invention, the compound of the formula I or II is administered in combination with a sulfonylurea such as, for example, tolbutamide, glibenclamide, glipizide or glimepiride.

In one embodiment of the invention, the compound of the formula I or II is administered in combination with a biguanide such as, for example, metformin.

In another embodiment of the invention, the compound of the formula I or II is administered in combination with a meglitinide such as, for example, repaglinide or nateglinide.

In one embodiment of the invention, the compound of the formula I or II is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinyl-methoxy]phenyl]methyl]-2,4-thiazolidinedione.

In one embodiment of the invention, the compound of the formula I or II is administered in combination with an α-glucosidase inhibitor such as, for example, miglitol or acarbose.

In one embodiment of the invention, the compound of the formula I or II is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of the formula I or II is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment of the invention, the compound of the formula I or II is administered in combination with an inhibitor of glycogen phosphorylase, such as, for example, PSN-357 or FR-258900 or those as described in WO 2003/084922, WO 2004/007455, WO 2005/073229-31 or WO 2005/067932.

In one embodiment of the invention, the compound of the formula I or II is administered in combination with glucagon receptor antagonists such as, for example, A-770077, NNC-25-2504 or as described in WO 2004/100875 or WO 2005/065680.

In one embodiment of the invention, the compound of the formula I or II is administered in combination with activators of glucokinase, such as, for example, RO-4389620, LY-2121260 (WO 2004/063179), PSN-105, PSN-110, GKA-50 or those as are described for example by Prosidion in WO 2004/072031, WO 2004/072066, WO 05/103021 or WO 06/016178, by Roche in WO 00/058293, WO 00/183465, WO 00/183478, WO 00/185706, WO 00/185707, WO 01/044216, GB 02385328, WO 02/008209, WO 02/014312, WO 02/46173, WO 02/48106, DE 10259786, WO 03/095438, US 04067939 or WO 04/052869, by Novo Nordisk in EP 1532980, WO 03/055482, WO 04/002481, WO 05/049019, WO 05/066145 or WO 05/123132, by Merck/Banyu in WO 03/080585, WO 03/097824, WO 04/081001, WO 05/063738 or WO 05/090332, by Eli Lilly in WO 04/063194, or by Astra Zeneca in WO 01/020327, WO 03/000262, WO 03/000267, WO 03/015774, WO 04/045614, WO 04/046139, WO 05/044801, WO 05/054200, WO 05/054233, WO 05/056530, WO 05/080359, WO 05/080360 or WO 05/121110.

In one embodiment of the invention, the compound of the formula I or II is administered in combination with an inhibitor of gluconeogenesis, such as, for example, FR-225654.

In one embodiment of the invention, the compound of the formula I or II is administered in combination with inhibitors of fructose-1,6-bisphosphatase (FBPase), such as, for example, CS-917.

In one embodiment of the invention, the compound of the formula I or II is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment of the invention, the compound of the formula I or II is administered in combination with inhibitors of glutamine-fructose-6-phosphate amidotransferase (GFAT), as are described for example in WO 2004/101528.

In one embodiment of the invention, the compound of the formula I or II is administered in combination with inhibitors of dipeptidylpeptidase IV (DPP-IV), such as, for example, vildagliptin (LAF-237), sitagliptin (MK-0431), saxagliptin (BMS-477118), GSK-823093, PSN-9301, SYR-322, SYR-619, TA-6666, TS-021, GRC-8200, GW-825964X or as are described in WO 2003/074500, WO 2003/106456, WO 2004/50658, WO 2005/058901, WO 2005/012312, WO 2005/012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment of the invention, the compound of the formula I or II is administered in combination with inhibitors of 11-beta-hydroxysteroid dehydrogenase 1 (11β-HSD1), such as, for example, BVT-2733 or those as are described for example in WO 2001/90090-94, WO 2003/43999, WO 2004/112782, WO 2003/44000, WO 2003/44009, WO 2004/112779, WO 2004/113310, WO 2004/103980, WO 2004/112784, WO 2003/065983, WO 2003/104207, WO 2003/104208, WO 2004/106294, WO 2004/011410, WO 2004/033427, WO 2004/041264, WO 2004/037251, WO 2004/056744, WO 2004/065351, WO 2004/089367, WO 2004/089380, WO 2004/089470-71, WO 2004/089896, WO 2005/016877 or WO 2005/097759.

In one embodiment of the invention, the compound of the formula I or II is administered in combination with inhibitors of protein tyrosine phosphatase 1B (PTP1B), as are described for example in WO 2001/19830-31, WO 2001/17516, WO 2004/506446, WO 2005/012295, PCT/EP2005/005311, PCT/EP2005/005321, PCT/EP2005/007151, PCT/EP2005/01294 or DE 10 2004 060542.4.

In one embodiment of the invention, the compound of the formula I or II is administered in combination with modulators of the sodium-dependent glucose transporter 1 or 2 (SGLT1, SGLT2), such as, for example, KGA-2727, T-1095 and SGL-0010 or as are described for example in WO 2004/

007517, WO 2004/52903, WO 2004/52902, WO 2005/121161, WO 2005/085237, JP2004359630 or by A. L. Handlon in Expert Opin. Ther. Patents (2005) 15(11), 1531-1540.

In one embodiment of the invention, the compound of the formula I or II is administered in combination with inhibitors of hormone-sensitive lipase (HSL) as described for example in WO 01/17981, WO 01/66531, WO 2004/035550, WO 2005/073199 or WO 03/051842.

In one embodiment of the invention, the compound of the formula I or II is administered in combination with inhibitors of acetyl-CoA carboxylase (ACC), such as, for example, those as described in WO 1999/46262, WO 2003/72197, WO 2003/072197 or WO 2005/044814.

In one embodiment of the invention, the compound of the formula I or II is administered in combination with an inhibitor of phosphoenolpyruvate carboxykinase (PEPCK), such as, for example, those as described in WO 2004/074288.

In one embodiment of the invention, the compound of the formula I or II is administered in combination with an inhibitor of glycogen synthase kinase-3 beta (GSK-3 beta), as described for example in US2005222220, WO 2004/046117, WO 2005/085230, WO 2005/111018, WO 2003/078403, WO 2004/022544, WO 2003/106410, WO 2005/058908, US2005038023, WO 2005/009997, US2005026984, WO 2005/000836, WO 2004/106343, EP1460075, WO 2004/014910, WO 2003/076442, WO 2005/087727 or WO 2004/046117.

In one embodiment of the invention, the compound of the formula I or II is administered in combination with an inhibitor of protein kinase C beta (PKC beta), such as, for example, ruboxistaurin.

In one embodiment of the invention, the compound of the formula I or II is administered in combination with an endothelin A receptor antagonist such as, for example, avosentan (SPP-301).

In one embodiment of the invention, the compound of the formula I or II is administered in combination with inhibitors of "I-kappaB kinase" (IKK inhibitors), as are described for example in WO 2001/000610, WO 2001/030774, WO 2004/022553 or WO 2005/097129.

In one embodiment of the invention, the compound of the formula I or II is administered in combination with modulators of the glucocorticoid receptor, like those described for example in WO 2005/090336.

In a further embodiment of the invention, the compound of the formula I or II is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);
NPY antagonists such as, for example, naphthalene-1-sulfonic acid {4-[(4-amino-quinazolin-2-ylamino)methyl]cyclohexylmethyl}amide hydrochloride (CGP 71683A);
peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO 2005/080424;
cannabinoid receptor 1 antagonists such as, for example, rimonabant, SR147778 or those as are described for example in EP 0656354, WO 00/15609, WO 02/076949, WO 2005/080345, WO 2005/080328, WO 2005/080343, WO 2005/075450, WO 2005/080357, WO 2001/70700, WO 2003/026647-48, WO 2003/02776, WO 2003/040107, WO 2003/007887, WO 2003/027069, U.S. Pat. No. 6,509,367, WO 2001/32663, WO 2003/086288, WO 2003/087037, WO 2004/048317, WO 2004/058145, WO 2003/084930, WO 2003/084943, WO 2004/058744, WO 2004/013120, WO 2004/029204, WO 2004/035566, WO 2004/058249, WO 2004/058255, WO 2004/058727, WO 2004/069838, US20040214837, US20040214855, US20040214856, WO 2004/096209, WO 2004/096763, WO 2004/096794, WO 2005/000809, WO 2004/099157, US20040266845, WO 2004/110453, WO 2004/108728, WO 2004/000817, WO 2005/000820, US20050009870, WO 2005/00974, WO 2004/111033-34, WO 2004/11038-39, WO 2005/016286, WO 2005/007111, WO 2005/007628, US20050054679, WO 2005/027837, WO 2005/028456, WO 2005/063761-62, WO 2005/061509 or WO 2005/077897;
MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO 2005/060985, WO 2005/009950, WO 2004/087159, WO 2004/078717, WO 2004/078716, WO 2004/024720, US20050124652, WO 2005/051391, WO 2004/112793, WOUS20050222014, US20050176728, US20050164914, US20050124636, US20050130988, US20040167201, WO 2004/005324, WO 2004/037797, WO 2005/042516, WO 2005/040109, WO 2005/030797, US20040224901, WO 2005/01921, WO 2005/09184, WO 2005/000339, EP1460069, WO 2005/047253, WO 2005/047251, EP1538159, WO 2004/072076, WO 2004/072077 or WO 2006/024390;
orexin receptor antagonists (e.g. 1-(2-methylbenzoxazol-6-yl)-3-[1,5]naphthyridin-4-ylurea hydrochloride (SB-334867-A) or those as are described for example in WO 2001/96302, WO 2001/85693, WO 2004/085403 or WO 2005/075458); histamine H3 receptor agonists (e.g. 3-cyclohexyl-1-(4,4-dimethyl-1,4,6,7-tetrahydroimidazo[4,5-c]pyridin-5-yl)propan-1-one oxalic acid salt (WO 00/63208) or those as are described in WO 2000/64884, WO 2005/082893);
CRF antagonists (e.g. [2-methyl-9-(2,4,6-trimethylphenyl)-9H-1,3,9-triazafluoroen-4-yl]dipropylamine (WO 00/66585));
CRF BP antagonists (e.g. urocortin);
urocortin agonists;
β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));
MSH (melanocyte-stimulating hormone) agonists;
MCH (melanin-concentrating hormone) receptor antagonists (such as, for example, NBI-845, A-761, A-665798, A-798, ATC-0175, T-226296, T-71, GW-803430 or compounds such as are described in WO 2003/15769, WO 2005/085200, WO 2005/019240, WO 2004/011438, WO 2004/012648, WO 2003/15769, WO 2004/072025, WO 2005/070898, WO 2005/070925, WO 2006/018280, WO 2006/018279, WO 2004/039780, WO 2003/033476, WO 2002/006245, WO 2002/002744, WO 2003/004027 or FR2868780);
CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), SR-146131 (WO 02/44150) or SSR-125180); serotonin reuptake inhibitors (e.g. dexfenfluramine);
mixed serotoninergic and noradrenergic compounds (e.g. WO 00/71549);

5-HT receptor agonists, e.g. 1-(3-ethylbenzofuran-7-yl)piperazine oxalic acid salt (WO 01/09111);

5-HT2C receptor agonists (such as, for example, APD-356, BVT-933 or those as are described in WO 2000/77010, WO 2007/7001-02, WO 2005/019180, WO 2003/064423, WO 2002/42304 or WO 2005/082859);

5-HT6 receptor antagonists as are described for example in WO 2005/058858;

bombesin receptor agonists (BRS-3 agonists);

galanin receptor antagonists;

growth hormone (e.g. human growth hormone or AOD-9604);

growth-hormone-releasing compounds (tertiary butyl 6-benzyloxy-1-(2-diisopropyl-aminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO 2005/030734;

TRH agonists (see, for example, EP 0 462 884);

uncoupling protein 2 or 3 modulators;

leptin agonists (see, for example, Lee, Daniel W.; Leinung, Matthew C.;

Rozhayskaya-Arena, Marina; Grasso, Patricia. Leptin agonists as a potential approach to the treatment of obesity. Drugs of the Future (2001), 26(9), 873-881); DA agonists (bromocriptine or Doprexin);

lipase/amylase inhibitors (like those described for example in WO 00/40569);

inhibitors of diacylglycerol O-acyltransferases (DGATs) as described for example in US2004/0224997, WO 2004/094618, WO 2000/58491, WO 2005/044250, WO 2005/072740, JP2005/206492 or WO 2005/013907;

inhibitors of fatty acid synthase (FAS) such as, for example, C75 or those as described in WO 2004/005277;

oxyntomodulin;

oleoyl-estrone or thyroid hormone receptor agonists such as, for example: KB-2115 or those as described in WO 2005/8279, WO 2001/72692, WO 2001/94293, WO 2003/084915, WO 2004/018421 or WO 2005/092316.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment of the invention, the further active ingredient is dexamphetamine or amphetamine.

In one embodiment of the invention, the further active ingredient is fenfluramine or dexfenfluramine.

In another embodiment of the invention, the further active ingredient is sibutramine.

In one embodiment of the invention, the further active ingredient is mazindole or phentermine.

In one embodiment of the invention, the compound of the formula I or II is administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6)). Caromax is a carob-containing product from Nutrinova, Nutrition Specialties & Food Ingredients GmbH, Industriepark Hoechst, 65926 Frankfurt/Main). Combination with Caromax® is possible in one preparation or by separate administration of compounds of the formula I or II and Caromax®. Caromax® can in this connection also be administered in the form of food products such as, for example, in bakery products or muesli bars.

In one embodiment of the invention, the compound of the formula I or II is administered in combination with PDE inhibitors (phosphodiesterase), like those described for example in WO 2003/077949 or WO 2005/012485.

In one embodiment of the invention, the compound of the formula I or II is administered in combination with NAR-1 (nicotinic acid receptor) agonists like those described for example in WO 2004/094429.

In one embodiment of the invention, the compound of the formula I or II is administered in combination with CB2 (cannabinoid receptor) agonists like those described for example in US2005/143448.

In one embodiment of the invention, the compound of the formula I or II is administered in combination with histamine-1 agonists like those described for example in WO 2005/101979.

In one embodiment of the invention, the compound of the formula I or II is administered in combination with bupropion as described in WO 2006/017504.

In one embodiment of the invention, the compound of the formula I or II is administered in combination with opioid antagonists like those described for example in WO 2005/107806 or WO 2004/094429.

In one embodiment of the invention, the compound of the formula I or II is administered in combination with neutral endopeptidase inhibitors like those described for example in WO 2002/02513, WO 2002/06492, WO 2002/040008, WO 2002/040022 or WO 2002/047670.

In one embodiment of the invention, the compound of the formula I or II is administered in combination with NPY inhibitors (neuropeptide Y) like those described for example in WO 2002/047670.

In one embodiment of the invention, the compound of the formula I or II is administered in combination with sodium/hydrogen exchange inhibitors like those described for example in WO 2003/092694.

In one embodiment of the invention, the compound of the formula I or II is administered in combination with modulators of the glucocorticoid receptor like those described for example in WO 2005/090336.

In one embodiment of the invention, the compound of the formula I or II is administered in combination with nicotine receptor agonists like those described for example in WO 2004/094429.

In one embodiment of the invention, the compound of the formula I or II is administered in combination with NRIs (norepinephrine reuptake inhibitors) like those described for example in WO 2002/053140.

In one embodiment of the invention, the compound of the formula I or II is administered in combination with MOA (E-beta-methoxyacrylate) such as, for example, segeline or like those described for example in WO 2002/053140.

In one embodiment of the invention, the compound of the formula I or II is administered in combination with antithrombotic active ingredients such as, for example, clopidogrel.

It will be appreciated that every suitable combination of the compounds of the invention with one or more of the aforementioned compounds and optionally one or more other pharmacologically active substances is regarded as falling within the protection conferred by the present invention.

Some of the formulae for the development codes mentioned above are detailed hereinafter.

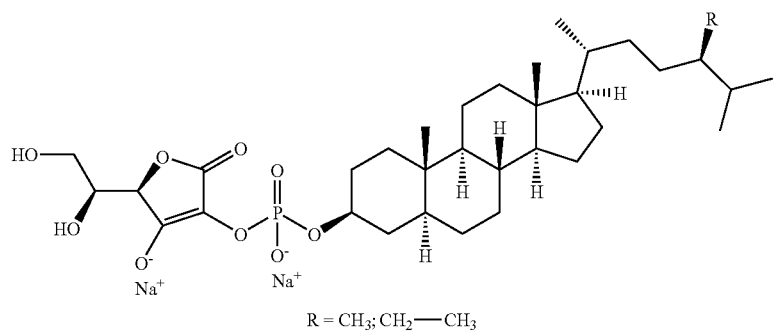
R = CH₃; CH₂—CH₃
FM-VP4
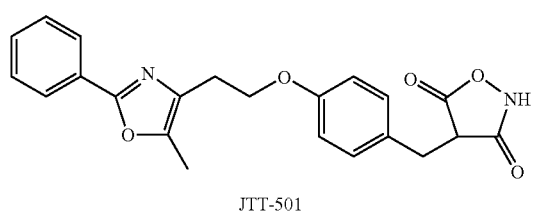
JTT-501
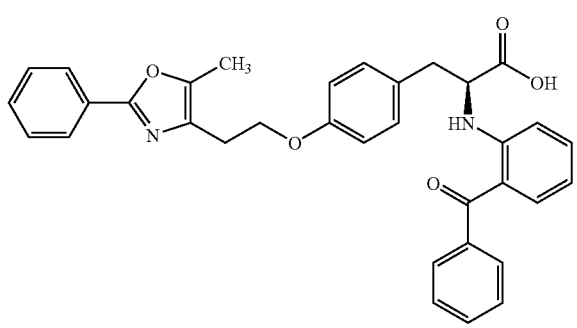
GI 262570
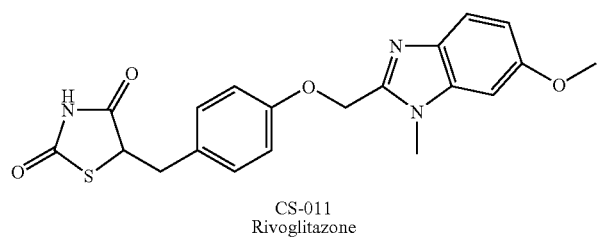
CS-011
Rivoglitazone
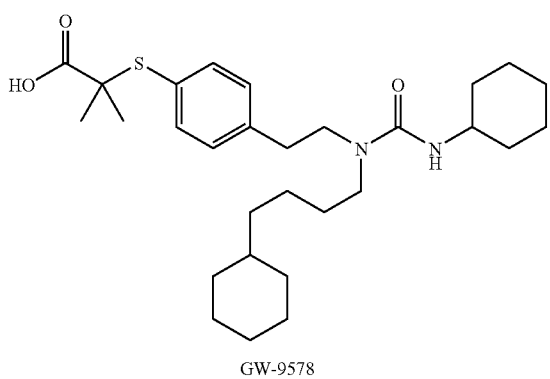
GW-9578
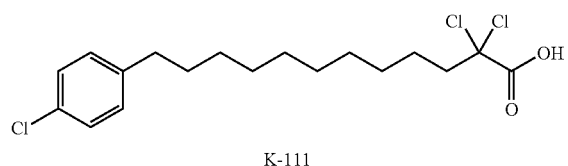
K-111
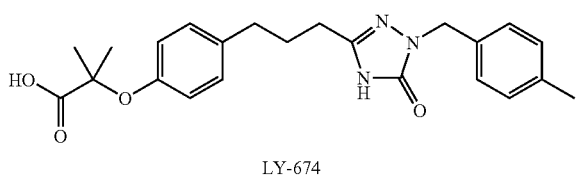
LY-674
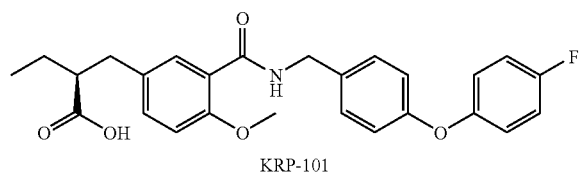
KRP-101
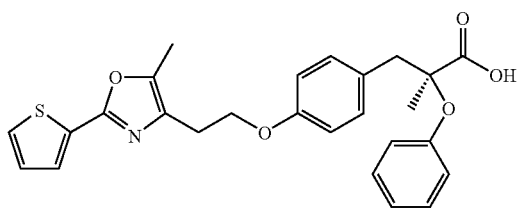
LY-510929

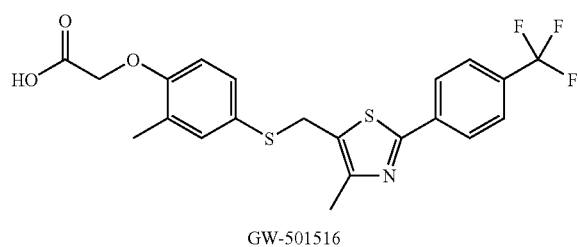
GW-501516
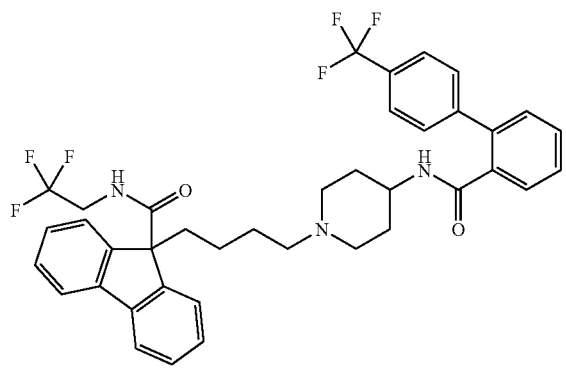
BMS-201038
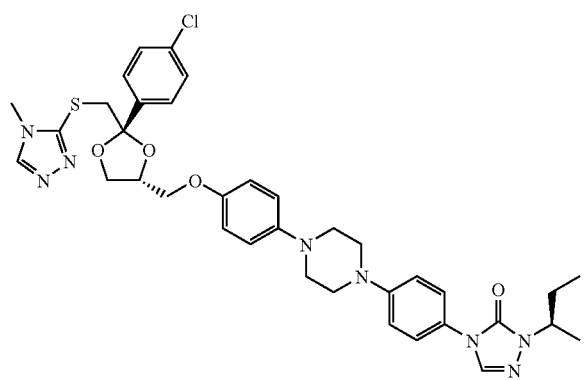
R-103757
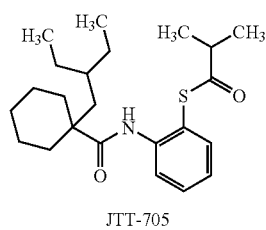
JTT-705
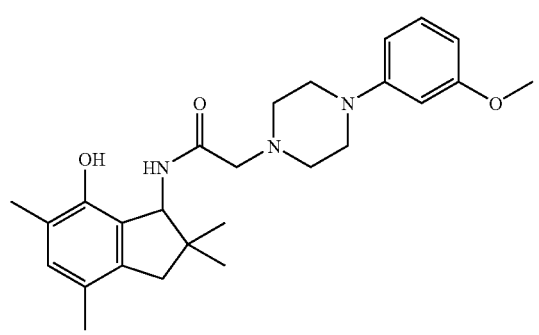
OPC-14117
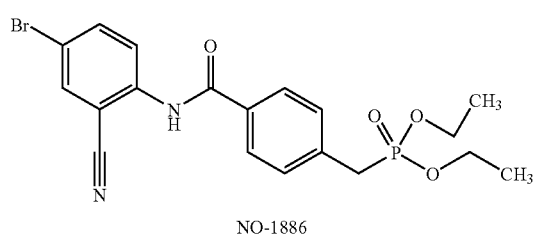
NO-1886
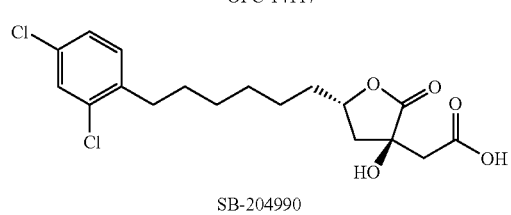
SB-204990
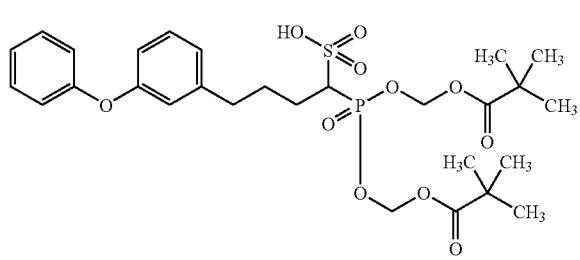
BMS-188494
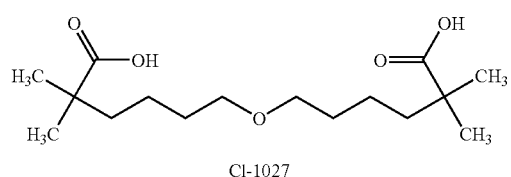
CI-1027
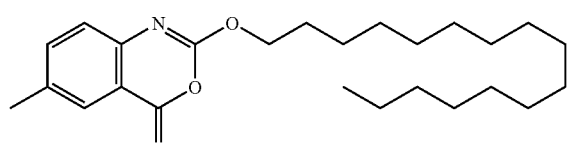
ATL-962

25
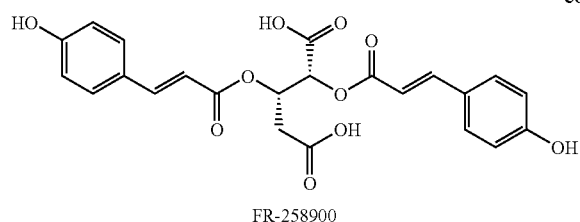
FR-258900
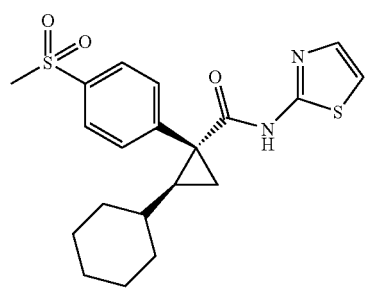
LY-2121260
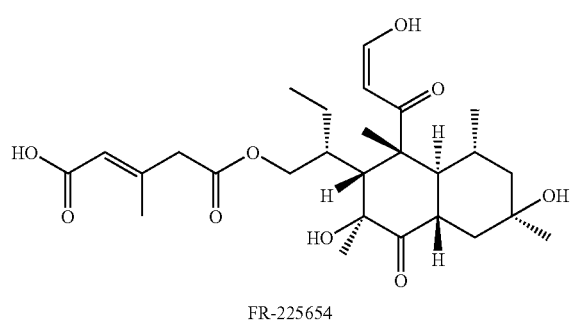
FR-225654
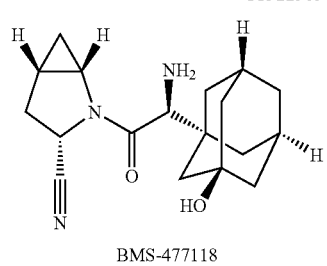
BMS-477118
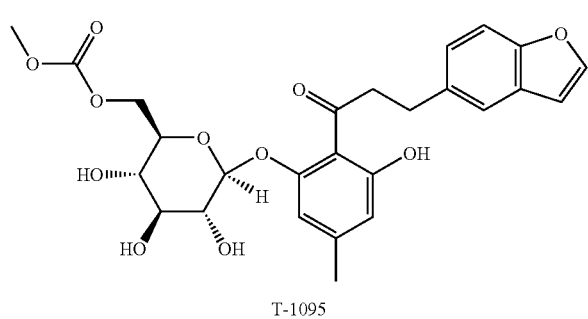
T-1095
26
-continued
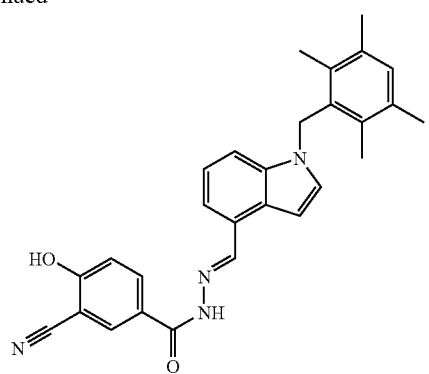
NNC-25-2504
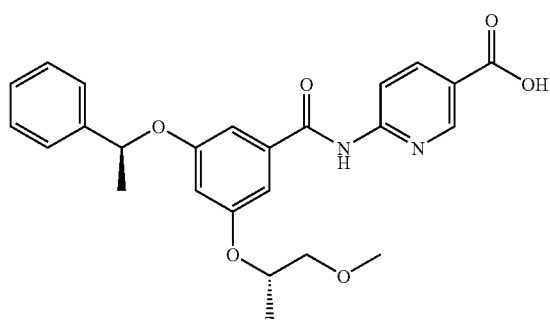
GKA-50
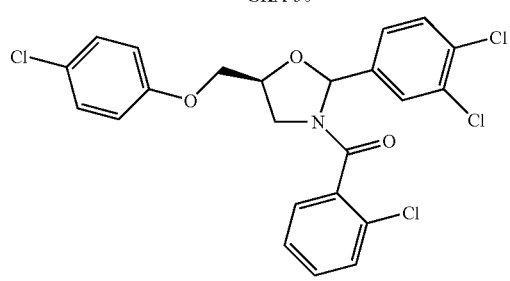
KST-48
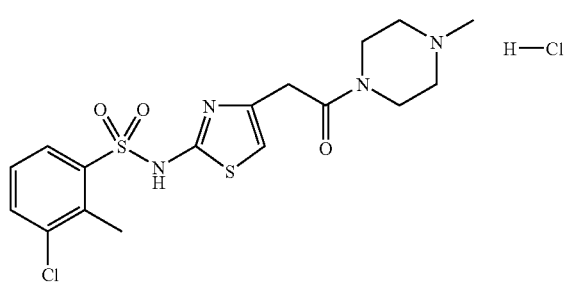
BVT-2733
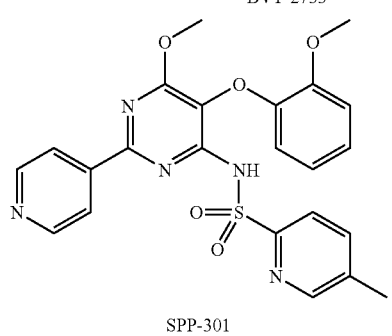
SPP-301

-continued
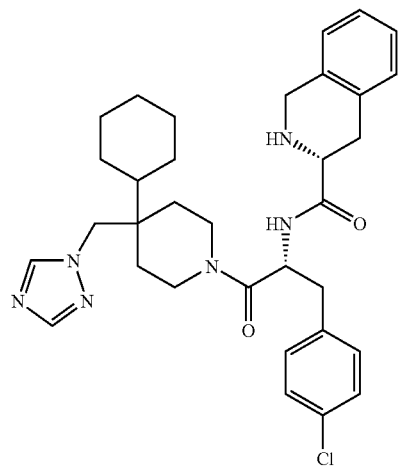
THIQ
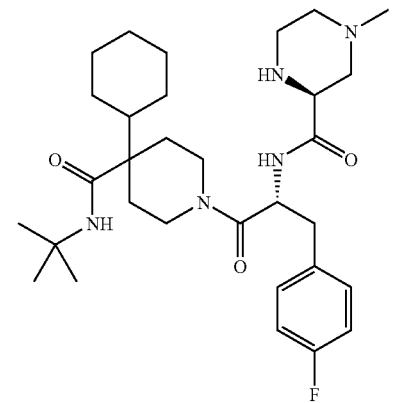
MB243
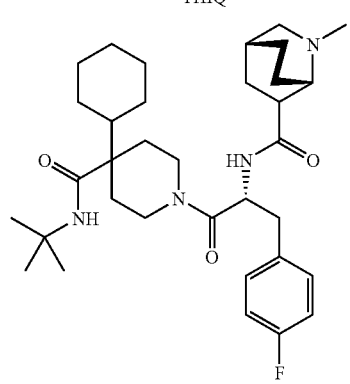
RY764
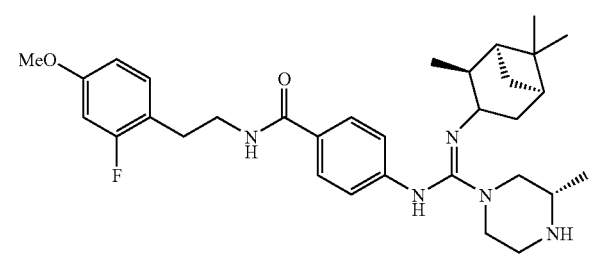
CHIR-785
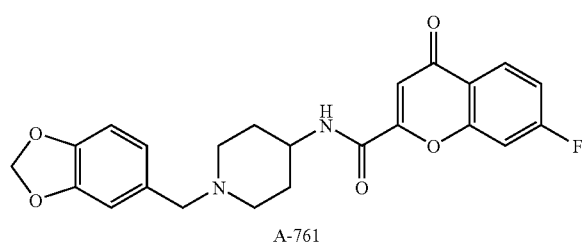
A-761
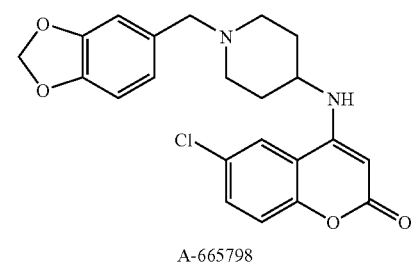
A-665798
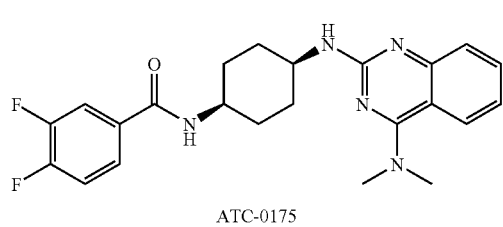
ATC-0175
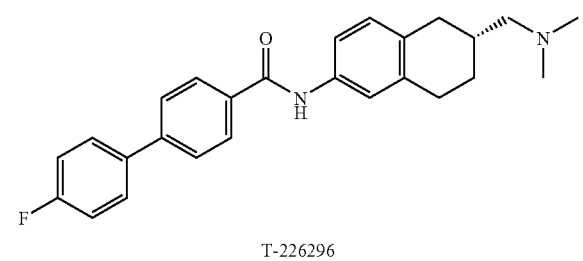
T-226296
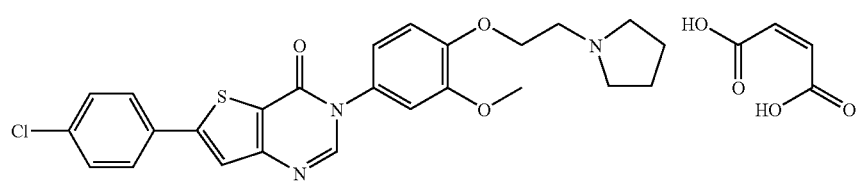
GW-803430

-continued

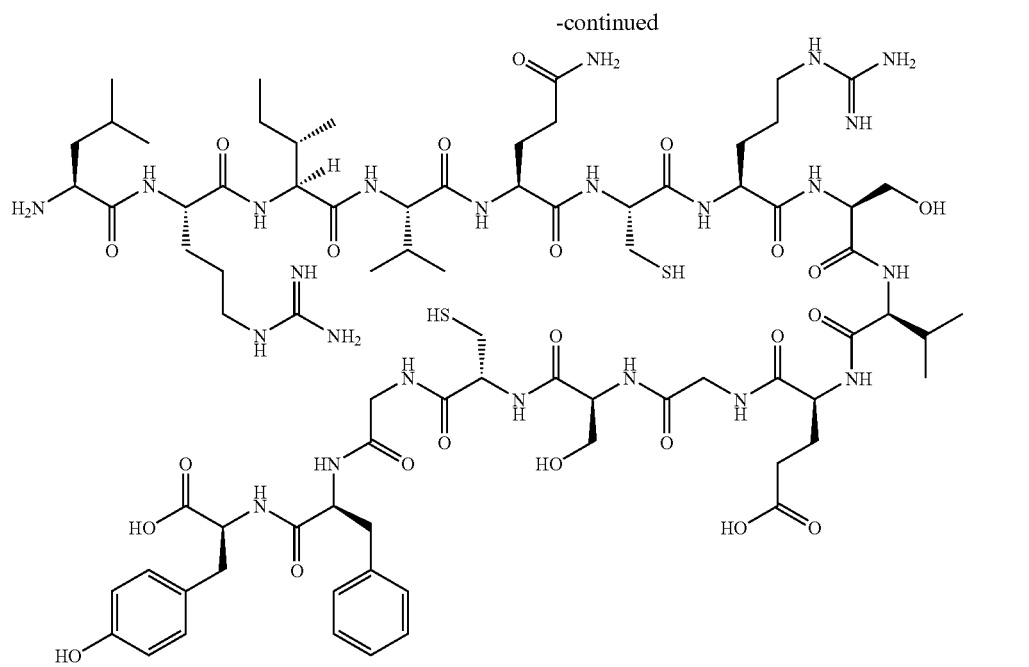

AOD-9604

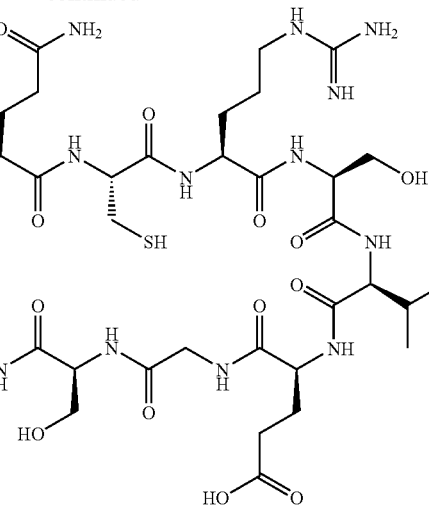

C75

A-778193

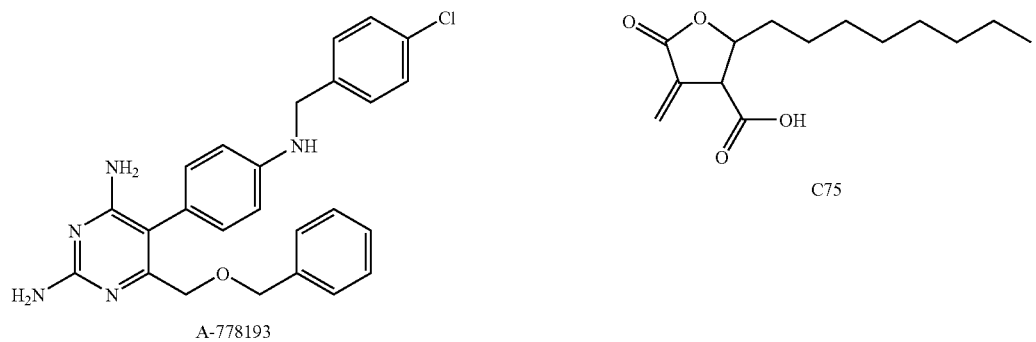

Oleoyl-estrone

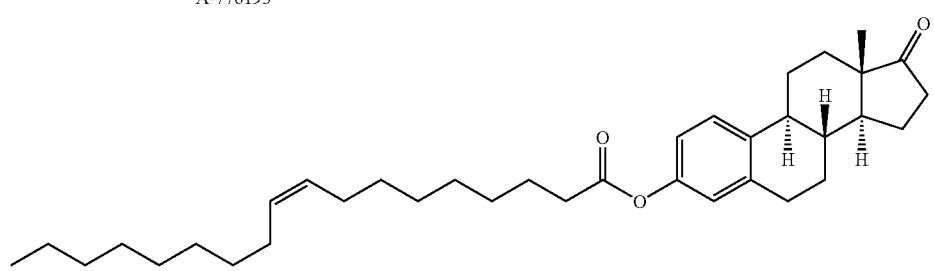

KB-2115

The activity of the compounds of the invention of the formulae I or II was tested in the following enzyme assay systems:

HSL Inhibition Assay

Preparation of the Partially Purified HSL:

Isolated rat fat cells are obtained from epididymal adipose tissue from untreated male rats (Wistar, 220-250 g) by collagenase treatment in accordance with published methods (e.g. S. Nilsson et al., Anal. Biochem. 158, 1986, 399-407; G. Fredrikson et al., J. Biol. Chem. 256, 1981, 6311-6320; H. Tornquist et al., J. Biol. Chem. 251, 1976, 813-819). The fat cells from 10 rats are washed three times by flotation with 50 ml of homogenization buffer (25 ml Tris/HCl, pH 7.4, 0.25 M sucrose, 1 mM ETDA, 1 mM DTT, 10 µg/ml leupeptin, 10

μg/ml antipain, 20 μg/ml pepstatin) each time and finally taken up in 10 ml of homogenization buffer. The fat cells are homogenized in a Teflon-in-glass homogenizer (Braun-Melsungen) by 10 strokes at 1500 rpm and 15° C. The homogenate is centrifuged (Sorvall SM24 tubes, 5000 rpm, 10 min, 4° C.). The subnatant between the layer of fat at the top and the pellet is removed and the centrifugation is repeated. The subnatant resulting therefrom is centrifuged again (Sorvall SM24 tubes, 20 000 rpm, 45 min, 4° C.). The subnatant is removed, and 1 g of heparin-Sepharose (Pharmacia-Biotech, CL-6B, washed 5× with 25 mM Tris/HCl, pH 7.4, 150 mM NaCl) is added. After incubation at 4° C. for 60 min (shaking at intervals of 15 min), the mixture is centrifuged (Sorvall SM24 tubes, 3000 rpm, 10 min, 4° C.). The supernatant is adjusted to pH 5.2 by adding glacial acetic acid and is incubated at 4° C. for 30 min. The precipitates are collected by centrifugation (Sorvall SS34, 12 000 rpm, 10 min, 4° C.) and suspended in 2.5 ml of 20 mM Tris/HCl, pH 7.0, 1 mM EDTA, 65 mM NaCl, 13% sucrose, 1 mM DTT, 10 mg/ml leupeptin/pepstatin/antipain. The suspension is dialyzed against 25 mM Tris/HCl, pH 7.4, 50% glycerol, 1 mM DTT, 10 μg/ml leupeptin, pepstatin, antipain at 4° C. overnight and then loaded onto a hydroxiapatite column (0.1 g per 1 ml of suspension, equilibrated with 10 mM potassium phosphate, pH 7.0, 30% glycerol, 1 mM DTT). The column is washed with four volumes of equilibration buffer at a flow rate of 20 to 30 ml/h. The HSL is eluted with one volume of equilibration buffer containing 0.5 M potassium phosphate and then dialyzed (see above) and concentrated 5- to 10-fold by ultrafiltration (Amicon Diaflo PM 10 Filter) at 4° C. The partially purified HSL can be stored at −70° C. for 4 to 6 weeks.

HSL Activity Assay:

To prepare the substrate, 25-50 μCi of [3H]trioleoylglycerol (in toluene), 6.8 μmol of unlabeled trioleoylglycerol and 0.6 mg of phospholipids (phosphatidylcholine/phosphatidylinositol 3:1 w/v) are mixed, dried with $N_2$ and then taken up in 2 ml of 0.1 M KPi (pH 7.0) by ultrasound treatment (Branson 250, microtip, setting 1-2, 2×1 min with an interval of 1 min). After addition of 1 ml of KPi and renewed ultrasound treatment (4×30 sec on ice with intervals of 30 sec), 1 ml of 20% BSA (in KPi) is added (final concentration of trioleoylglycerol 1.7 mM). For the reaction, 100 μl of substrate solution are pipetted into 100 μl of HSL solution (HSL prepared as above, diluted in 20 mM KPi, pH 7.0, 1 mM EDTA, 1 mM DTT, 0.02% BSA, 20 μg/ml pepstatin, 10 μg/ml leupeptin) and incubated at 37° C. for 30 min. Addition of 3.25 ml of methanol/chloroform/heptane (10:9:7) and of 1.05 ml of 0.1 M $K_2CO_3$, 0.1 M boric acid (pH 10.5) is followed by thorough mixing and finally centrifugation (800×g, 20 min). After phase separation, one equivalent of the upper phase (1 ml) is removed and the radioactivity is determined by liquid scintillation measurement.

Substances are normally tested in four independent mixtures. The inhibition of the HSL enzymatic activity by a test substance is determined by comparing with an uninhibited control reaction. The $IC_{50}$ is calculated from an inhibition plot with at least 10 concentrations of the test substance. The GRAPHIT, Elsevier-BIOSOFT software package is used to analyze the data.

EL Inhibition Assay:

EL is released as secretory protein in high concentration into cell culture medium (conditioned medium) by recombinant cell lines (CHO, HEK293). This is employed as enzyme solution after concentration.

The phospholipase-specific substrate 1,2-bis(4,4-difluoro-5,7-dimethyl-4-bora-3a,4a-diaza-s-indacene-3-undecanoyl)-sn-glycero-3-phosphocholine, (manufacturer Molecular Probes) is used to characterize the enzymatic activity of endothelial lipase and the effect of inhibitors. Hydrolysis of the A1 ester linkage of this phospholipid by the enzyme liberates the fluorescent dye Bodipy which can be detected after separation by thin-layer chromatography on an HPTLC plate (silica gel 60, Merck) or directly in the reaction vessel by measuring the fluorescence.

The substrate solution is prepared by taking up 100 μg of 1,2-bis(4,4-difluoro-5,7-dimethyl-4-bora-3a,4a-diaza-s-indacene-3-undecanoyl)-sn-glycero-3-phospho-choline (manufacturer Molecular Probes), 2.4 mg of tripalmitin (Sigma) and 7.9 mg of DOP-choline (1,2-dioleoyl-sn-glycero-3-phosphocholine) in 393 μl of chloroform and then transferring 157 μl into a fresh reaction vessel. After evaporation of the solvent, the lipid mixture is dissolved in 4 ml of 200 mM TRIS-HCl, 150 mM sodium chloride, pH=7.4, by sonication twice. The subsequent enzymic reaction takes place at 37° C. for 60 minutes. For this purpose, 45 μl of the substrate solution are incubated with 1 μl of inhibitor of appropriate concentration (dissolved in DMSO, pure DMSO solution is used as control) and 5 μl of enzyme solution (conditioned medium). Then 3 μl of the assay mixture are loaded onto an HPTLC plate (silica gel 60, Merck), and the liberated fluorescent dye is separated for detection with an eluent (diethyl ether:petroleum benzene:acetic acid [78:22:1]). After evaporation of the eluent, the plate is read in a fluorescence scanner. An increased release of the fluorescent dye in the uninhibited reaction is to be observed as a measure of the enzymic activity.

The enzymatic activity is reduced as a function of the inhibitor concentration used, and the inhibitor concentration at which a half-maximum enzymatic activity is observed is called $IC_{50}$.

In these assays, the compounds of the examples showed the following $IC_{50}$ values:

| Example | $IC_{50}$ [μM] HSL | $IC_{50}$ [μM] EL |
|---|---|---|
| 1a | 0.32 | |
| 1b | 0.62 | |
| 2 | 1.11 | |
| 9b | 1.15 | |
| 10a | | 0.05 |
| 10b | | 0.06 |
| 11a | | 0.26 |
| 11b | | 1.47 |
| 12 | | 0.22 |
| 13 | | 0.84 |
| 14 | 1.0 | |
| 15 | 1.5 | |
| 16 | 0.58 | |

Preparation Processes

The compounds of the invention of the formulae I or II are prepared by methods known per se, e.g. by acylation of substituted or unsubstituted indazole derivatives III with carbamoyl chlorides IV (method A), or in two stages by reacting indazole derivatives III with phosgene or equivalents such as trichloromethyl chlorocarbonate, ditrichloromethyl carbonate or 4-nitrophenyl chloroformate and further reaction of the resulting indazolecarboxylic acid derivative with an amine V (method B). For compounds in which R2 is hydrogen, the indazole derivatives III can also be reacted with the appropriate isocyanates VI R1-N=C=O.

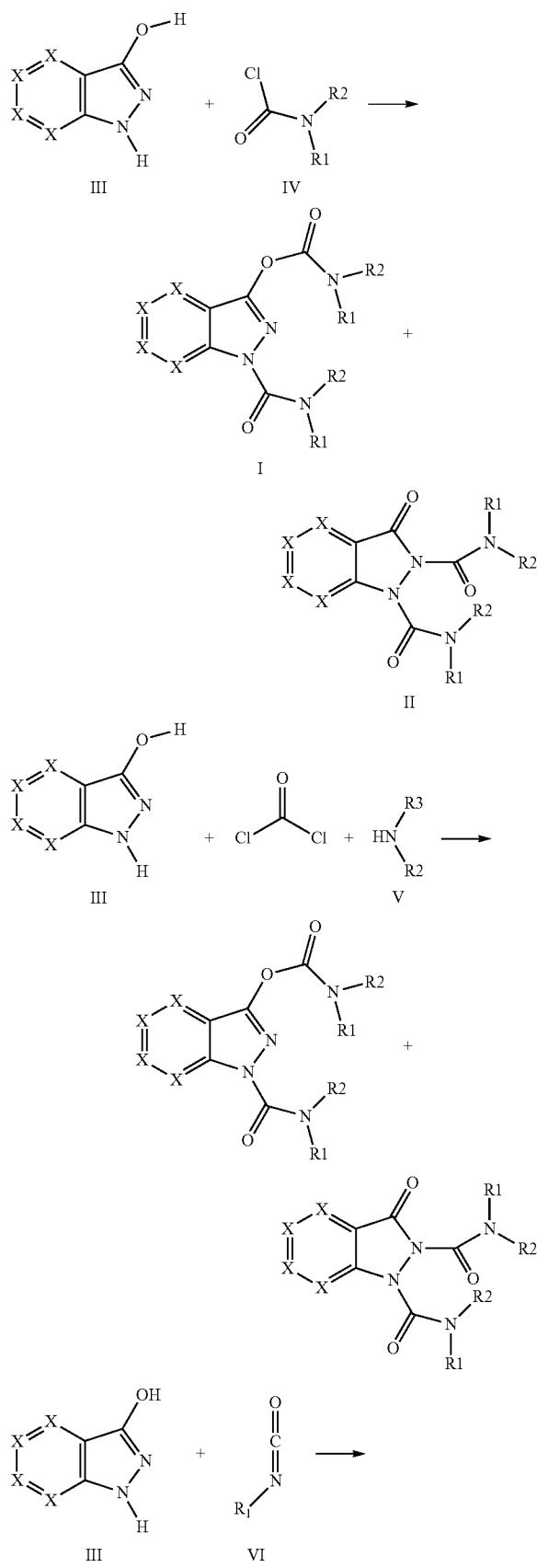

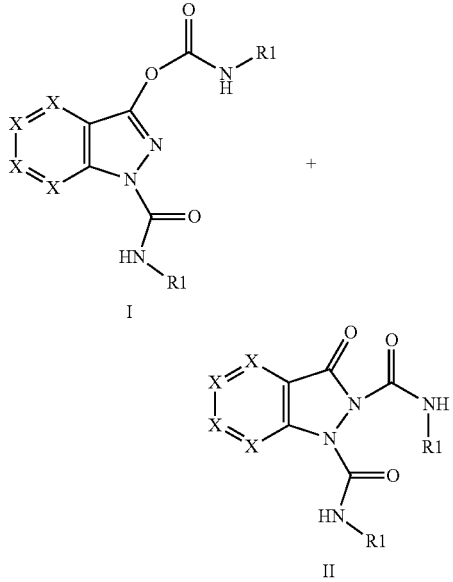

Since acids are usually liberated in these reactions, it is advisable to add bases such as pyridine, triethylamine, sodium hydroxide solution or alkali metal carbonates for expedition. The reactions can be carried out in wide temperature ranges. It has usually proved to be advantageous to operate at from 0° C. to the boiling point of the solvent used. Examples of solvents employed are methylene chloride, THF, DMF, toluene, ethyl acetate, n-heptane, dioxane, diethyl ether or pyridine. If anhydrous conditions are used, strong bases such as lithium hydride, sodium hydride or potassium tert-butoxide in aprotic solvents such as THF or DMF have also proved suitable.

The indazole derivatives employed as starting compounds III, or corresponding aza-substituted derivatives are commercially available or can be prepared by processes known from the literature (e.g. L. Baiocchi, G. Corsi Synthesis (1978), 633-648, I. Sekikawa et al. J. Het. Chem. (1973), 931-932).

The compounds of the formulae I and II obtained by the processes described above can be separated by known separation processes such as, for example, chromatographic processes.

The examples detailed below serve to illustrate the invention without, however, restricting it.

EXAMPLES

Example 1

6-Fluoro-1-(4-phenylpiperazine-1-carbonyl)-1H-indazol-3-yl 4-phenylpiperazine-1-carboxylate and 6-fluoro-1,2-bis(4-phenylpiperazine-1-carbonyl)-1,2-dihydroindazol-3-one (1b)

200 mg (1.315 mmol) of 6-fluoro-1H-indazol-3-ol were dissolved in 5 ml of pyridine. Addition of 365 µl (2.63 mmol) of triethylamine and 355 mg (1.56 mmol) of 4-phenylpiperazine-1-carbonyl chloride was followed by stirring at room temperature for 3 h. Addition of 730 µl of triethylamine and 177 mg of 4-phenylpiperazine-1-carbonyl chloride was followed by stirring for a further 20 h. The reaction mixture was concentrated and mixed with water and ethyl acetate, and the organic phase was separated off, concentrated and purified by preparative HPLC (PR18, acetonitrile/water 0.1% TFA). Yield: 12 mg (2%), M+H+: 529.34, 6-fluoro-1-(4-phenylpiperazine-1-carbonyl)-1H-indazol-3-yl 4-phenylpiperazine-1-carboxylate; 30 mg, (4%), M+H+: 529.40, 6-fluoro-1,2-bis(4-phenylpiperazine-1-carbonyl)-1,2-dihydroindazol-3-one. It was additionally possible to isolate 6-fluoro-1H-indazol-3-yl 4-phenylpiperazine-1-carboxylate as compound not of the invention.

Example 2

1-(6,7-Dihydro-4H-thieno[3,2-c]pyridine-5-carbonyl)-6-fluoro-1H-indazol-3-yl 6,7-dihydro-4H-thieno[3,2-c]pyridine-5-carboxylate In analogy to example 1, 200 mg (1.315 mmol) of 6-fluoro-1H-indazol-3-ol were reacted with 318 mg (1.578 mmol) of 6,7-dihydro-4H-thieno[3,2-c]pyridine-5-carbonyl chloride.
Yield: 18 mg (3%), M+H+: 483.25.

Example 3

6-Fluoro-1-(thiomorpholine-4-carbonyl)-1H-indazol-3-yl thiomorpholine-4-carboxylate In analogy to example 1, 200 mg (1.315 mmol) of 6-fluoro-1H-indazol-3-ol were reacted with 261.4 mg (1.578 mmol) of thiomorpholine-4-carbonyl chloride.
Yield: 39 mg (7%), M+H+: 411.17.

Example 4

6-Fluoro-1-(4-trifluoromethylpiperidine-1-carbonyl)-1H-indazol-3-yl 4-trifluoromethylpiperidine-1-carboxylate In analogy to example 1, 200 mg (1.315 mmol) of 6-fluoro-1H-indazol-3-ol were reacted with 340 mg (1.578 mmol) of 4-trifluoromethylpiperidine-1-carbonyl chloride.
Yield: 8 mg (1%), M+H+: 511.36.

Example 5

1-(2,6-Dimethylmorpholine-4-carbonyl)-6-fluoro-1H-indazol-3-yl 2,6-dimethylmorpholine-4-carboxylate In analogy to example 1, 200 mg (1.315 mmol) of 6-fluoro-1H-indazol-3-ol were reacted with 280.3 mg (1.578 mmol) of 2,6-dimethylmorpholine-4-carbonyl chloride.
Yield: 16 mg (3%), M+H+: 435.29.

Example 6

4,6-Difluoro-1-(4-methylpiperidine-1-carbonyl)-1H-indazol-3-yl 4-methylpiperidine-1-carboxylate and 4,6-difluoro-1,2-bis(4-methylpiperidine-1-carbonyl)-1,2-dihydroindazol-3-one In analogy to example 1, 60 mg (0.35 mmol) of 4,6-difluoro-1H-indazol-3-ol were reacted with 85.6 mg (0.53 mmol) of 4-methylpiperidine-1-carbonyl chloride.
Yield: 73 mg (49%), M+H+: 421.35 4,6-difluoro-1-(4-methylpiperidine-1-carbonyl)-1H-indazol-3-yl 4-methylpiperidine-1-carboxylate and 3 mg (2%), M+H+: 421.34 4,6-difluoro-1,2-bis(4-methylpiperidine-1-carbonyl)-1,2-dihydroindazol-3-one.

Example 7

1-(4-Methylpiperidine-1-carbonyl)-6-trifluoromethyl-1H-pyrazolo[3,4-b]pyridin-3-yl 4-methylpiperidine-1-carboxylate In analogy to example, 1, 120 mg (0.59 mmol) of 6-trifluoromethyl-1H-pyrazolo-[3,4-b]pyridin-3-ol were reacted with 143.3 mg (0.89 mmol) of 4-methylpiperidine-1-carbonyl chloride. Yield: 71 mg (26%), M+H+: 454.27.

Example 8

6-Chloro-4-methyl-1-(4-methylpiperidine-1-carbonyl)-1H-pyrazolo[3,4-b]pyridin-3-yl 4-methylpiperidine-1-carboxylate In analogy to example 1, 1.2 g (6.54 mmol) of 6-chloro-4-methyl-1H-pyrazolo-[3,4-b]pyridin-3-ol were reacted with 1.29 g (7.98 mmol) of 4-methylpiperidine-1-carbonyl chloride. Yield: 238 mg (8%), M+H+: 434.27.

Example 9

6-Fluoro-1,2-bis(4-methylpiperidine-1-carbonyl)-1,2-dihydroindazol-3-one (9a) and 6-fluoro-1-(4-methylpiperidine-1-carbonyl)-1H-indazol-3-yl 4-methylpiperidine-1-carboxylate (9b)

In analogy to example 1, 10 g (65.73 mmol) of 6-fluoro-1H-indazol-3-ol were reacted with 11.69 g (72.3 mmol) of 4-methylpiperidine-1-carbonyl chloride. Yield: 455 mg (1.7%), M+H+: 403.14, 6-fluoro-1,2-bis(4-methylpiperidine-1-carbonyl)-1,2-dihydroindazol-3-one and 1.6 g (6%), M+H+: 403.18, 6-fluoro-1-(4-methylpiperidine-1-carbonyl)-1H-indazol-3-yl 4-methylpiperidine-1-carboxylate.

Example 10

6-Chloro-3-oxo-3H-indazole-1,2-dicarboxylic acid bishexylamide (10a) and 6-chloro-1-hexylcarbamoyl-1H-indazol-3-yl hexylcarbamate (10b)

100 mg (0.59 mmol) of 6-chloro-1H-indazol-3-ol were dissolved in 5 ml of DMF. Addition of 83 mg (0.65 mmol) of 1-isocyanatohexane was followed by stirring at room temperature for 1.5 h and at 50° C. for 1 h, concentration and purification by preparative HPLC (PR18, acetonitrile/water 0.1% TFA). Yield: 17 mg (7%), M+H+: 296.14, 6-chloro-3-oxo-3H-indazole-1,2-dicarboxylic acid bishexylamide and 12 mg (5%) of 6-chloro-1-hexylcarbamoyl-1H-indazol-3-yl hexylcarbamate. It was additionally possible to isolate 6-chloro-3-hydroxyindazole-1-carboxylic acid hexylamide as compound not according to the invention.

Example 11

6-Chloro-3-oxo-3H-indazole-1,2-dicarboxylic acid bisbenzylamide (11a) and 1-benzylcarbamoyl-6-chloro-1H-indazol-3-yl benzyl carbamate (11b)

In analogy to example 10, 100 mg (0.59 mmol) of 6-chloro-1H-indazol-3-ol were reacted with 86.85 mg (0.65 mmol) of isocyanatomethylbenzene. Yield: 31 mg (12%) of 6-chloro-3-oxo-3H-indazole-1,2-dicarboxylic acid bisbenzylamide, and 15 mg (6%) of 1-benzylcarbamoyl-6-chloro-1H-indazol-3-yl benzylcarbamate.

Example 12

1-(4-Methylpiperidine-1-carbonyl)-3-oxo-1,3-dihydroindazole-2-carboxylic acid 2-methylbenzylamide 105 mg (0.78 mmol) of 1H-indazol-3-ol were reacted in 3 ml of THF with 138.3 mg (0.94 mmol) of 1-isocyanatomethyl-2-methylbenzene to give 3-oxo-1,3-dihydroindazole-2-carboxylic acid 2-methylbenzylamide. 50 mg (178 µmol) of this compound were stirred in 3 ml of pyridine with 40 mg (355 µmol) of triethylamine and 43 mg (266 µmmol) of 4-methylpiperidine-1-carbonyl chloride at room temperature for 7 h. Addition of a further 120 mg of 4-methylpiperidine-1-carbonyl chloride and 100 mg of triethylamine in 3 portions was followed by stirring again for 7 h, concentration and purification by preparative HPLC (PR18, acetonitrile/water 0.1% TFA). Yield: 48 mg (66%), M+H+: 407.15.

Example 13

3-Oxo-3H-indazole-1,2-dicarboxylic acid bis(2-methylbenzylamide)

In analogy to example 11, 300 mg (2.24 mmol) of 1H-indazol-3-ol were reacted with 395.5 mg (2.69 mmol) of 1-isocyanatomethyl-2-methylbenzene. Yield: 177 mg (18%), M+H+: 429.26.

Example 14

6-Amino-1-(4-trifluoromethylpiperidine-1-carbonyl)-1H-indazol-3-yl-4-methylpiperidine-1-carboxylate In analogy to example 12, 35.66 mg (0.13 mmol) of 6-amino-1H-indazol-3-yl 4-methylpiperidine-1-carboxylate were reacted with 33.63 mg (0.16 mmol) of 4-trifluoromethylpiperidine-1-carbonyl chloride. Yield: 10 mg (17%), M+H+: 454.13.

Example 15

6-Hydroxy-4-methyl-1-(4-methylpiperazine-1-carbonyl)-1H-pyrazolo[3,4-b]pyridin-3-yl 4-trifluoromethylpiperidine-1-carboxylate; as trifluoroacetate In analogy to example 12, 79.88 mg (0.23 mmol) of 6-hydroxy-4-methyl-1H-pyrazolo[3,4-b]pyridin-3-yl 4-trifluoromethylpiperidine-1-carboxylate were reacted with 41.3 mg (0.2 mmol) of 4-methylpiperazine-1-carbonyl chloride hydrochloride.
Yield: 18 mg (16%), M+H+: 471.35.

Example 16

6-Hydroxy-4-methyl-1-(4-trifluoromethylpiperidine-1-carbonyl)-1H-pyrazolo-[3,4-b]pyridin-3-yl 4-methylpiperidine-1-carboxylate In analogy to example 12, 99.87 mg (0.344 mmol) of 6-hydroxy-4-methyl-1H-pyrazolo[3,4-b]pyridin-3-yl 4-methylpiperidine-1-carboxylate were reacted with 83.4 mg (0.52 mmol) of 4-trifluoromethylpiperidine-1-carbonyl chloride. Yield: 16 mg (10%), M+H+: 470.20.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:
1. A compound of the formulae I or II:

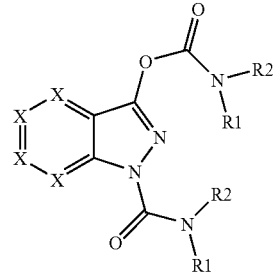

(I)

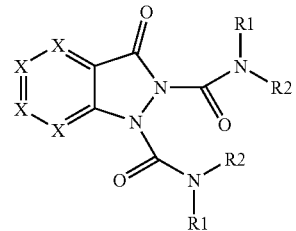

(II)

wherein

X is identically or differently =C(—R)— or =N—, where only one X is =N—;

R is identically or differently hydrogen, halogen, ($C_1$-$C_6$)-alkyl, ($C_1$-$C_3$)-alkyloxy-($C_1$-$C_3$)-alkylene, ($C_1$-$C_3$)-haloalkyl, hydroxy, ($C_1$-$C_6$)-alkylmercapto, amino, ($C_1$-$C_6$)-alkylamino, di-($C_2$-$C_{12}$)-alkylamino, mono-($C_1$-$C_6$)-alkylaminocarbonyl, di-($C_2$-$C_8$)-alkylaminocarbonyl, COOR3, cyano, ($C_1$-$C_6$)-alkylsulfonyl, alkylsulfinyl, aminosulfonyl, nitro, pentafluorosulfanyl, phenyl, heterocycle, phenoxy, O-heterocycle, CO—NR6R7, O—CO—NR6R7, O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—NR6R7 or unsubstituted or mono- or poly-F-substituted ($C_1$-$C_6$)-alkyloxy;

R1 is identically or differently ($C_5$-$C_{16}$)-alkyl, ($C_3$-$C_{12}$)-cycloalkyl, Y-aryl, Y-heterocycle or bicycle, where cycloalkyl, aryl, heterocycle or bicycle are optionally substituted one or more times by halogen, ($C_1$-$C_6$)-alkyl, ($C_1$-$C_3$)-alkyloxy, hydroxy, ($C_1$-$C_6$)-alkylmercapto, amino, ($C_1$-$C_6$)-alkylamino, di-($C_2$-$C_{12}$)-alkylamino, mono-($C_1$-$C_6$)-alkylaminocarbonyl, di-($C_2$-$C_8$)-alkylaminocarbonyl, ($C_1$-$C_6$)-alkyloxycarbonyl, ($C_1$-$C_6$)-alkylcarbonyl, cyano, trifluoromethyl, trifluoromethyloxy, ($C_1$-$C_6$)-alkylsulfonyl, aminosulfonyl, and nitro;

Y is ($C_1$-$C_3$)-alkyl, which is optionally substituted one or more times by halogen, ($C_1$-$C_3$)-alkyl, hydroxy or trifluoromethyl;

R2 is hydrogen; or

R1 and R2 together with the nitrogen atom carrying them form a monocyclic, saturated or partly unsaturated 4- to 7-membered ring system or a bicyclic saturated or partly unsaturated 8- to 14-membered ring system whose individual members of the ring systems are optionally replaced by one to three atoms or atomic groups from the series —CHR4-, —CR4R5-, —(C=R4)-, —NR4-, —C(=O)—, —O—, —S—, —SO—, —SO$_2$—, with the proviso that two units from the series —O—, —S—, —SO—, —SO$_2$— are not adjacent to each other;

R3 is hydrogen, ($C_1$-$C_6$)-alkyl or benzyl;

R4, R5 are identically or differently $(C_1-C_6)$-alkyl, halogen, trifluoromethyl, phenyl, heterocycle, COOR3 or $(C_3-C_{12})$-cycloalkyl; and R6, R7 are identically or differently hydrogen, $(C_1-C_6)$-alkyl, phenyl, benzyl or $(C_3-C_{12})$-cycloalkyl; or a tautomer thereof or a physiologically tolerated salt thereof, with the proviso that not more than one R is phenyl or heterocycle.

2. The compound of the formulae I or II as claimed in claim 1, wherein:

X is identically or differently =C(—R)— or =N—, where only one X is =N—;

R is identically or differently hydrogen, halogen, $(C_1-C_6)$-alkyl, hydroxy, $(C_1-C_3)$-alkyloxy, amino, COOR3, trifluoromethyl, $(C_1-C_6)$-alkylsulfonyl, nitro, pentafluorosulfanyl, phenyl, $(C_5-C_7)$-heterocycle, CO—NR6R7, O—CO—NR6R7 or O—CO—$(C_1-C_6)$-alkylene-CO—O—$(C_1-C_6)$-alkyl;

R1 is identically or differently $(C_6-C_{10})$-alkyl, $(C_6-C_{12})$-cycloalkyl, Y-phenyl or Y-heterocycle or bicycle, where cycloalkyl, phenyl, heterocycle or bicycle are optionally substituted one or more times by halogen, $(C_1-C_6)$-alkyl, $(C_1-C_3)$-alkyloxy, hydroxy, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkyloxycarbonyl, $(C_1-C_6)$-alkylcarbonyl, cyano, trifluoromethyl, trifluoromethyloxy, $(C_1-C_6)$-alkylsulfonyl, aminosulfonyl or nitro;

Y is —CH$_2$—, which is optionally substituted once by fluorine, methyl or hydroxy;

R2 is hydrogen; or

R1 and R2 together with the nitrogen atom carrying them form a monocyclic, saturated 5- to 6-membered ring system or a bicyclic saturated or partly unsaturated 9- to 10-membered ring system, whose individual members of the ring systems are optionally replaced by one to three atoms or atomic groups from the series —CHR4-, —CR4R5-, —(C=R4)-, —NR4-, —O— or —S—, with the proviso that two units from the series —O— or —S— are not adjacent to each other;

R3 is hydrogen, $(C_1-C_6)$-alkyl or benzyl;

R4, R5 are identically or differently $(C_1-C_6)$-alkyl, halogen, trifluoromethyl, COOR3, $(C_3-C_7)$-cycloalkyl, phenyl or heterocycle; and R6, R7 are identically or differently hydrogen, $(C_1-C_6)$-alkyl, phenyl, benzyl or $(C_3-C_{12})$-cycloalkyl; or a tautomer thereof or a physiologically tolerated salt thereof, with the proviso that not more than one R is phenyl or $(C_5-C_7)$-heterocycle.

3. The compound of the formulae I or II as claimed in claim 1, wherein:

X is identically or differently =C(—R)— or =N—, where only one X is =N—;

R is identically or differently hydrogen, halogen, hydroxy, $(C_1-C_6)$-alkyl, trifluoromethyl, $(C_1-C_3)$-alkyloxy or amino;

R1 is identically or differently $(C_6-C_{10})$-alkyl, $(C_6-C_{12})$-cycloalkyl, Y-phenyl or Y-heterocycle, where cycloalkyl, phenyl, or heterocycle are optionally substituted one or more times by halogen, $(C_1-C_6)$-alkyl, $(C_1-C_3)$-alkyloxy, hydroxy, amino, trifluoromethyl or trifluoromethyloxy;

Y is —CH$_2$—;

R2 is hydrogen; or

R1 and R2 together with the nitrogen atom carrying them form a monocyclic, saturated 5- to 6-membered ring system or a bicyclic saturated or partly unsaturated 9- to 10-membered ring system, whose individual members of the ring systems are optionally replaced by one to three atoms or atomic groups from the series —CHR4-, —CR4R5-, —(C=R4)-, —NR4-, —O— or —S—, with the proviso that two units from the series —O— or —S— are not adjacent to each other;

R3 is hydrogen, $(C_1-C_6)$-alkyl or benzyl; and

R4, R5 are identically or differently $(C_1-C_6)$-alkyl, halogen, trifluoromethyl, COOR3, $(C_3-C_7)$-cycloalkyl, phenyl or $(C_5-C_7)$-heterocycle; or a tautomer thereof or a physiologically tolerated salt thereof.

4. The compound of the formulae I or II as claimed in claim 1 wherein:

X is identically or differently =C(—R)— or =N—, where only one X is =N—;

R is identically or differently hydrogen, halogen, hydroxy, $(C_1-C_6)$-alkyl, trifluoromethyl, $(C_1-C_3)$-alkyloxy or amino;

R1 is identically or differently $(C_6-C_{10})$-alkyl or Y-phenyl, which is optionally substituted by halogen, $(C_1-C_6)$-alkyl, $(C_1-C_3)$-alkyloxy or trifluoromethyl;

Y is CH$_2$;

R2 is hydrogen; or

R1 and R2 together with the nitrogen atom carrying them form a monocyclic, saturated 5- to 6-membered ring system, whose individual members are optionally replaced by one to three atoms or atomic groups from the series —CHR4-, —NR4-, —O— or —S—, with the proviso that two units from the series —O— or —S— are not adjacent to each other; and R4 is $(C_1-C_6)$-alkyl, cyclopropyl, trifluoromethyl or phenyl; or a tautomer thereof or a physiologically tolerated salt thereof.

5. The compound of the formulae I or II as claimed in claim 1, wherein:

X in position 4, 5 and 6 is identically or differently =C(—R)—, and in position 7 is =N—.

6. A pharmaceutical composition comprising one or more compounds of the formulae I or II as claimed in claim 1 or a pharmaceutically acceptable salt thereof in combination with at least one pharmaceutically acceptable excipient.

7. A pharmaceutical composition comprising one or more compounds of the formulae I or II as claimed in claim 2 or a pharmaceutically acceptable salt thereof in combination with at least one pharmaceutically acceptable excipient.

8. A pharmaceutical composition comprising one or more compounds of the formulae I or II as claimed in claim 3 or a pharmaceutically acceptable salt thereof in combination with at least one pharmaceutically acceptable excipient.

9. A pharmaceutical composition comprising one or more compounds of the formulae I or II as claimed in claim 4 or a pharmaceutically acceptable salt thereof in combination with at least one pharmaceutically acceptable excipient.

10. A pharmaceutical composition comprising one or more compounds of the formulae I or II as claimed in claim 5 or a pharmaceutically acceptable salt thereof in combination with at least one pharmaceutically acceptable excipient.

11. A method for the treatment of diabetes mellitus comprising administering to a patient in need of said treatment a therapeutically effective amount of a compound of the formulae I or II as claimed in claim 1 or a pharmaceutically acceptable salt thereof.

12. A method for the treatment of dyslipidemia comprising administering to a patient in need of said treatment a therapeutically effective amount of a compound of the formulae I or II as claimed in claim 1 or a pharmaceutically acceptable salt thereof.

13. A method for the treatment of atherosclerotic disorders comprising administering to a patient in need of said treatment a therapeutically effective amount of a compound of the formulae I or II as claimed in claim 1 or a pharmaceutically acceptable salt thereof.

14. A process for producing a medicament comprising one or more of the compounds of the formulae I or II as claimed in claim 1, which comprises mixing the latter with a pharmaceutically suitable carrier and converting this mixture into a form suitable for administration.

15. A process for preparing compounds of the formulae I or II as claimed in claim 1, which comprises:
   a) acylating an indazole derivative of the formula III with a carbamoyl chloride of the formula IV;
   or
   b) reacting in two stages initially with phosgene or an equivalent chosen from trichloromethyl chlorocarbonate, ditrichloromethyl carbonate or 4-nitrophenyl chloroformate and in a second step with an amine of formula V,
   in which X, R1, R2 and R3 are as defined in claim 1, and subsequently separating the compounds I and II

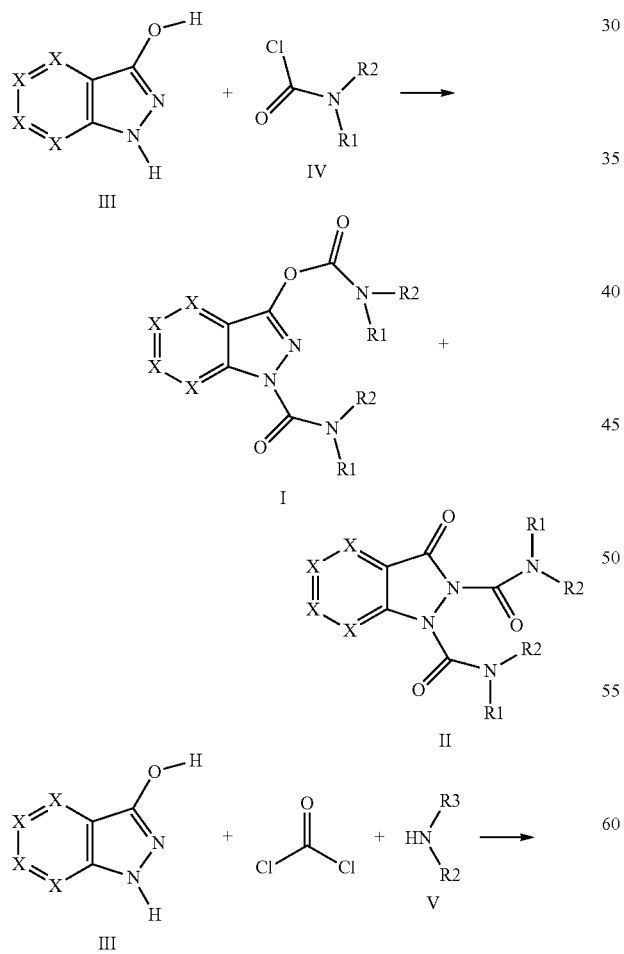

16. A process for preparing compounds of the formulae I or II as claimed in claim 1, wherein R2 is hydrogen, which comprises:
   reacting an indazole derivative of the formula III with isocyanate of the formula VI:
   O=C=N—R1, and subsequently separating the compounds I and II

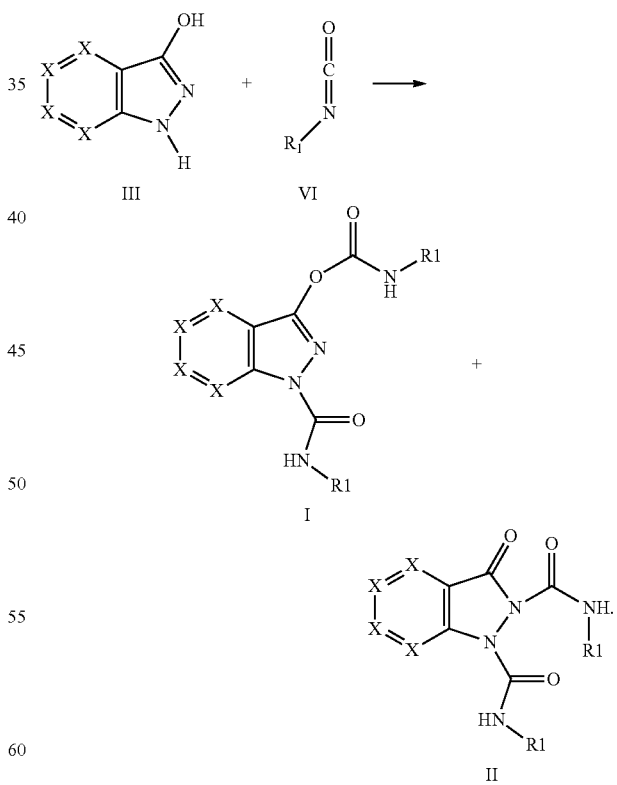

* * * * *